United States Patent
Pertel et al.

(10) Patent No.: US 11,781,248 B2
(45) Date of Patent: Oct. 10, 2023

(54) ANTI-TALEN ANTIBODIES AND USES THEREOF

(71) Applicant: ALLOGENE THERAPEUTICS, INC., South San Francisco, CA (US)

(72) Inventors: Thomas Charles Pertel, San Mateo, CA (US); Barbra Johnson Sasu, San Francisco, CA (US)

(73) Assignee: ALLOGENE THERAPEUTICS, INC., South San Francisco, CA (US)

( * ) Notice: Subject to any disclaimer, the term of this patent is extended or adjusted under 35 U.S.C. 154(b) by 519 days.

(21) Appl. No.: 16/900,602

(22) Filed: Jun. 12, 2020

(65) Prior Publication Data

US 2020/0392252 A1    Dec. 17, 2020

Related U.S. Application Data

(60) Provisional application No. 62/861,214, filed on Jun. 13, 2019.

(51) Int. Cl.
*C40B 40/10* (2006.01)
*C07K 16/40* (2006.01)
*C12N 15/63* (2006.01)

(52) U.S. Cl.
CPC .............. *C40B 40/10* (2013.01); *C07K 16/40* (2013.01); *C12N 15/63* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter |
| 5,789,538 A | 8/1998 | Rebar et al. |
| 5,821,337 A | 10/1998 | Carter et al. |
| 5,859,205 A | 1/1999 | Adair et al. |
| 5,869,619 A | 2/1999 | Stundnicka |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas et al. |
| 6,200,759 B1 | 3/2001 | Simon |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,534,261 B1 | 3/2003 | Cox et al. |

(Continued)

FOREIGN PATENT DOCUMENTS

| | | |
|---|---|---|
| WO | 1998037186 A1 | 8/1998 |
| WO | 1998053057 A1 | 11/1998 |

(Continued)

OTHER PUBLICATIONS

Menger, Laurie, et al., "TALEN-Mediated Inactivation of PD-1 in Tumor-Reactive Lymphocytes Promotes Intratumoral T-cell Persistence and Rejection of Established Tumors", Cancer Res; 76(8) Apr. 15, 2016, pp. 2087-2093.

(Continued)

*Primary Examiner* — Christian C Boesen
(74) *Attorney, Agent, or Firm* — Allogene Therapeutics, Inc.

(57) ABSTRACT

The present disclosure provides, among other things, antibodies for detecting TALENs and/or FokI nucleases in a sample and methods of using the same.

23 Claims, 1 Drawing Sheet

Specification includes a Sequence Listing.

(56) References Cited

U.S. PATENT DOCUMENTS

| | | |
|---|---|---|
| 6,881,557 B2 | 4/2005 | Foote |
| 7,709,226 B2 | 5/2010 | Foote |
| 9,322,037 B2 | 4/2016 | Liu et al. |
| 9,388,430 B2 | 7/2016 | Liu et al. |
| 9,834,791 B2 | 12/2017 | Zhang et al. |
| 2005/0215502 A1 | 9/2005 | Cox et al. |
| 2007/0134796 A1 | 6/2007 | Holmes et al. |
| 2010/0041074 A1 | 2/2010 | Kimura |
| 2011/0129481 A1 | 6/2011 | Cheong et al. |
| 2011/0200595 A1 | 8/2011 | Gerdes et al. |
| 2018/0086834 A1 | 3/2018 | Fournier et al. |

FOREIGN PATENT DOCUMENTS

| | | |
|---|---|---|
| WO | 2001088197 A1 | 11/2001 |
| WO | 2005084190 A2 | 9/2005 |
| WO | WO2013091903 A1 | 6/2013 |
| WO | WO2013093122 A2 | 6/2013 |
| WO | WO2014170257 A1 | 10/2014 |
| WO | 2014204578 A1 | 12/2014 |
| WO | WO2016016299 A1 | 2/2016 |
| WO | 2000027878 A1 | 5/2020 |

OTHER PUBLICATIONS

USPTO, "International Search Report & Written Opinion", mailed for PCT/US2020/037589 dated Jan. 26, 2021, 14 pages.

Menger, Laurie, et al., "TALEN-mediated genetic inactivation of the glucocorticoid receptor in cytomegalovirusspecific T cells"; Blood (2015) 126 (26): 2781-2789; https://doi.org/10.1182/blood-2015-08-664755.

EPO, Extended European Search Report dated Feb. 3, 2023, for EP application No. 20823120.9.

Al-Lazikani, Bissan, et al., "Standard Conformations for the Canonical Structures of Immunoglobulins", J. Mol. Biol. (1997) 273, 927-948.

Anderson, W. French, et al., "Human Gene Therapy", Science; May 8, 1992; vol. 256, Issue 5058; pp. 808-813; DOI: 10.1126/science.256.5058.808.

Ausubel, Frederick M., et al., "Short Protocols in Molecular Biology", A Compendium of Methods from Current Protocols in Molecular Biology; 4th ED.; Wiley and Sons, 1999; (TOC).

Beerli, Roger R., et al., "Engineering polydactyl zinc-finger transcription factors", Nat Biotechnol; Feb. 2002;20(2):135-41. doi: 10.1038/nbt0202-135.

Choo, Yen, et al., "Advances in zinc finger engineering", Current Opinion in Structural Biology; vol. 10, Issue 4, Aug. 1, 2000, pp. 411-416.

Chothia, Cyrus, et al., "Canonical structures for the hypervariable regions of immunoglobulins", J Mol Biol; Aug. 20, 1987;196(4):901-17. doi: 10.1016/0022-2836(87)90412-8.

Chothia, Cyrus, et al., "Structural Repertoire of the Human VH Segments", J. Mol. Biol. (1992) 227, 799-917.

Clark, Mike, "Antibody humanization: a case of the 'Emperor's new clothes'?", Immunol Today; . Aug. 2000;21(8):397-402. doi: 10.1016/s0167-5699(00)01680-7.

Collins, Mary, et al., "Gene therapy: progress and predictions", Proc Biol Sci; . Dec. 22, 2015;282(1821):20143003. doi: 10.1098/rspb.2014.3003.

Dall'Acqua, William F., et al., "Antibody humanization by framework shuffling", Methods; 2005 36(1):43-60; DOI: 10.1016/j.ymeth.2005.01.005.

Feuerbach, Frederick J., et al., "Progress in human gene therapy", Kidney International; vol. 49, Issue 6, Jun. 1996, pp. 1791-1794.

Holliger, Philipp, et al., ""Diabodies": Small bivalent and bispecific antibody fragments", Proc. Natl. Acad. Sci. USA, vol. 90, pp. 6444 6448, Jul. 1993, Biophysics.

Hwang, William Ying Khee, et al., "Use of human germline genes in a CDR homology-based approach to antibody humanization", Methods; . May 2005;36(1):35-42. doi: 10.1016/j.ymeth.2005.01.004.

Isalan, "A rapid, generally applicable method to engineer zinc fingers illustrated by targeting the HIV-1 promoter", Nat Biotechnol. Jul. 2001 ; 19(7): 656-660. doi:10.1038/90264.

Kabat, Elvin A., et al., "Sequences of Proteins of Immunological Interest", 5th Ed. NIH publication, No. 91-3242; 1992 (TOC).

Larrick, James W., et al., "Polymerase Chain REAmON Using Mixed Primers: Cloning of Human Monoclonal Antibody Variable Region Genes From Single Hybridoma Cells", Nature Biotechnology; 1989 7(9):934-938; DOI: 10.1038/nbt0989-934.

Liu, Alvin Y., "Chimeric mouse-human IgG1 antibody that can mediate lysis of cancer cells ", Proc Natl Acad Sci U S A. May 1987; 84(10): 3439 3443; doi: 10.1073/pnas.84.10.3439; 10.1073/pnas.84.10.3439.

Miller, A. Dusty, "Human gene therapy comes of age", Nature, 1992, vol. 357 (6378), 455-460; DOI: 10.1038/357455a0.

Pabo, Carl O., et al., "Design and selection of novel Cys2His2 zinc finger proteins", Annual Review of Biochemistry, 2001, vol. 70 (1), 313-340.

Padlan, Eduardo A, "Identification of specificity-determining residues in antibodies", FASEB J. Jan. 1995;9(1):133-9. doi: 10.1096/fasebj.9.1.7821752.

Poljak, Robert J., "Production and structure of diabodies", Structure Dec. 15, 1994, 2:1121-1123.

Rahman, Shamim H., et al., "Zinc-Finger Nucleases for Somatic Gene Therapy: The Next Frontier", Hum Gene Ther. Aug. 2011; 22(8): 925-933.

Riechmann, Lutz, et al., "Reshaping human antibodies for therapy", Nature, vol. 332, pp. 323-327, (1988).

Sambrook, J., et al., "Molecular Cloning: A Laboratory Manual", Second Ed., Cold Spring Harbor Laboratory Press, 1989 (TOC).

Segal, David J., et al., "Custom DNA-binding proteins come of age: polydactyl zinc-finger proteins", Current Opinion in Biotechnology; vol. 12, Issue 6, Dec. 1, 2001, pp. 632-637.

Tamura, Midori, et al., "Structural correlates of an anticarcinoma antibody: identification of specificity-determining residues (SDRs) and development of a minimally immunogenic antibody variant by retention of SDRs only", J Immunol; Feb. 1, 2000;164(3):1432-41. doi: 10.4049/jimmunol.164.3.1432.

Tramontano, Anna, et al., "Framework Residue 71 is a Major Determinant of the Position and Conformation of the Second Hypervariable Region in the V H Domains of Immunoglobulins", J. Mol. Biol. (1990) 215, 175-182.

Tsai, Shengdar Q., et al., "Dimeric CRISPR RNA-guided FokI nucleases for highly specific genome editing", Nat Biotechnol. Jun. 2014; 32(6): 569-576.

Urnov, Fyodor D., et al., "Genome editing with engineered zinc finger nucleases", Nat Rev Genet; . Sep. 2010;11(9):636-46. doi: 10.1038/nrg2842.

Winter, Greg, et al., "Humanized antibodies", Trends in Pharmacological Sciences; vol. 14, Issue 5, May 1993, pp. 139-143; DOI: 10.1016/0165-6147(93)90197-R.

Wolffe, Alan, "Chromatin Structure and Function 3rd Edition", Academic Press; 1998; pp. 456; ISBN: 9780127619156.

Zhang, Wei, et al., "Humanization of an anti-human TNF-alpha antibody by variable region resurfacing with the aid of molecular modeling", Mol Immunol;.Aug. 2005;42(12):1445-51. doi: 10.1016/j.molimm.2005.01.015. Epub Mar. 2, 2005.

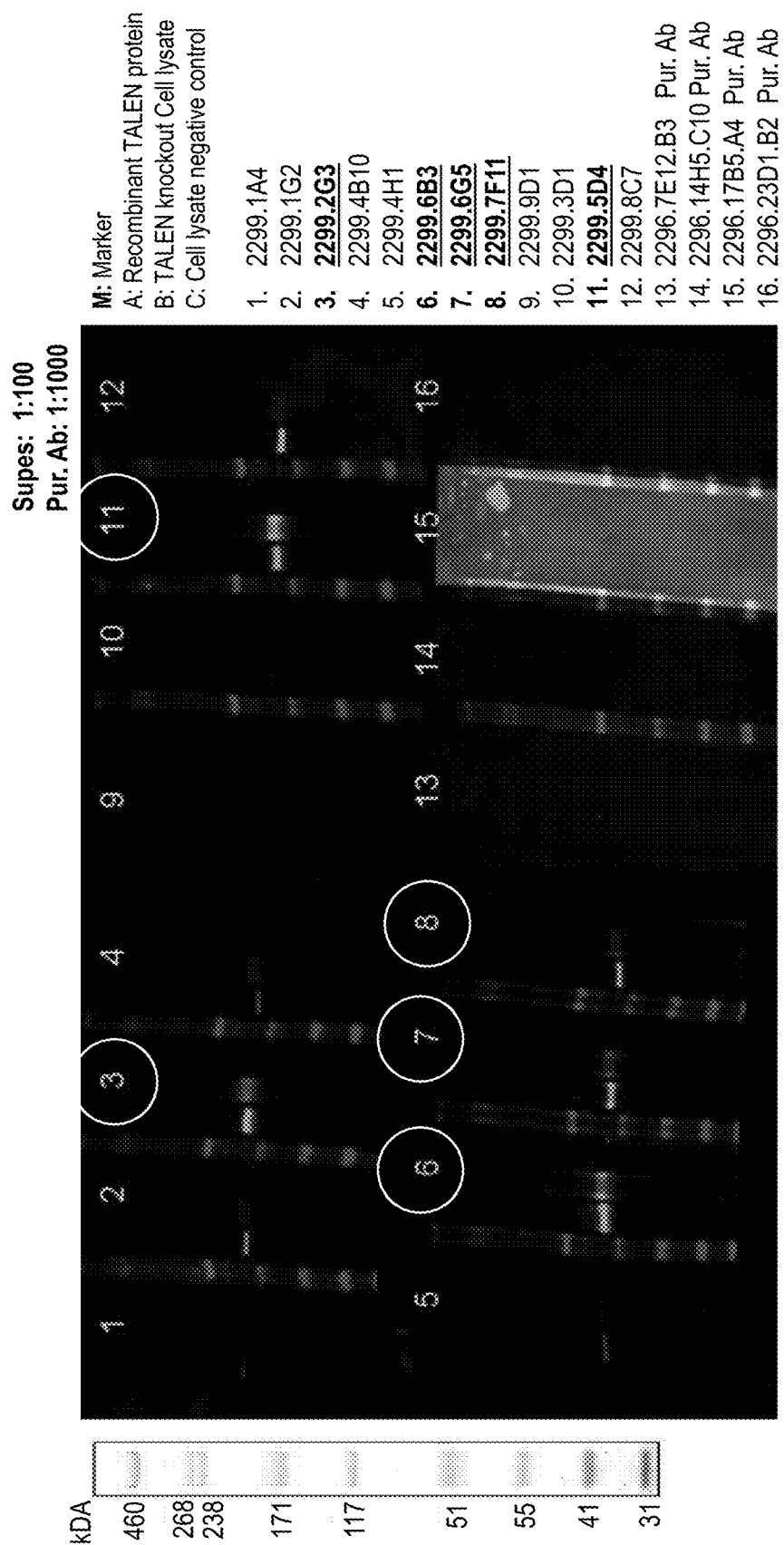

SEQUENCE LISTING

```
<160> NUMBER OF SEQ ID NOS: 38

<210> SEQ ID NO 1
<211> LENGTH: 154
<212> TYPE: PRT
<213> ORGANISM: Flavobacterium okeanokoites

<400> SEQUENCE: 1

Met Lys Val Met Glu Phe Phe Met Lys Val Tyr Gly Tyr Arg Gly Lys
1               5                   10                  15

His Leu Gly Gly Ser Arg Lys Pro Asp Gly Ala Ile Tyr Thr Val Gly
            20                  25                  30

Ser Pro Ile Asp Tyr Gly Val Ile Val Asp Thr Lys Ala Tyr Ser Gly
        35                  40                  45

Gly Tyr Asn Leu Pro Ile Gly Gln Ala Asp Glu Met Gln Arg Tyr Val
    50                  55                  60

Glu Glu Asn Gln Thr Arg Asn Lys His Ile Asn Pro Asn Glu Trp Trp
65                  70                  75                  80

Lys Val Tyr Pro Ser Ser Val Thr Glu Phe Lys Phe Leu Phe Val Ser
                85                  90                  95

Gly His Phe Lys Gly Asn Tyr Lys Ala Gln Leu Thr Arg Leu Asn His
            100                 105                 110

Ile Thr Asn Cys Asn Gly Ala Val Leu Ser Val Glu Glu Leu Leu Ile
        115                 120                 125

Gly Gly Glu Met Ile Lys Ala Gly Thr Leu Thr Leu Glu Glu Val Arg
    130                 135                 140

Arg Lys Phe Asn Asn Gly Glu Ile Asn Phe
145                 150

<210> SEQ ID NO 2
<211> LENGTH: 583
<212> TYPE: PRT
<213> ORGANISM: Flavobacterium okeanokoites

<400> SEQUENCE: 2

Met Phe Leu Ser Met Val Ser Lys Ile Arg Thr Phe Gly Trp Val Gln
1               5                   10                  15
```

```
Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
        275                 280                 285

Thr Arg Val Pro Lys Arg Val Tyr Trp Glu Met Leu Ala Thr Asn Leu
290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365

Tyr Gln Leu Lys Asp His Ile Leu Gln Phe Val Ile Pro Asn Arg Gly
370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
```

```
                      435                 440                 445
Gly Ser Arg Lys Pro Asp Gly Ala Ile Tyr Thr Val Gly Ser Pro Ile
    450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
        515                 520                 525

Lys Gly Asn Tyr Lys Ala Gln Leu Thr Arg Leu Asn His Ile Thr Asn
    530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580

<210> SEQ ID NO 3
<211> LENGTH: 120
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile His Trp Val Lys Gln Ala Pro Gly Glu Gly Leu Lys Trp Met
            35                  40                  45

Ala Trp Ile Asn Thr Glu Thr Gly Ala Pro Thr Phe Ala Asp Asp Phe
    50                  55                  60

Lys Gly Arg Leu Ala Leu Ser Leu Glu Thr Ser Ala Asn Thr Ala Tyr
65                  70                  75                  80

Leu Gln Ile Asn Asn Leu Lys His Glu Asp Thr Ala Thr Tyr Phe Cys
                85                  90                  95

Ala Lys Glu Gly Gly Phe Tyr Phe Tyr Ala Met Asp Tyr Trp Gly Gln
            100                 105                 110

Gly Thr Ser Val Thr Val Ser Ser
        115                 120

<210> SEQ ID NO 4
<211> LENGTH: 120
<212> TYPE: PRT
<213> ORGANISM: Mus musculus

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ala Phe Thr Asp Tyr
                20                  25                  30

Ser Ile His Trp Met Lys Gln Ala Pro Gly Glu Gly Leu Gln Trp Met
            35                  40                  45

Gly Trp Ile Asn Thr Glu Thr Ala Lys Pro Ala Phe Gly Asp Asp Phe
```

```
            50                  55                  60
Lys Gly Arg Phe Ala Phe Ser Leu Glu Thr Ser Ala Asn Thr Ala His
 65                  70                  75                  80

Leu His Ile Asn Asn Leu Arg Thr Glu Asp Thr Ala Thr Tyr Phe Cys
                 85                  90                  95

Ala Lys Glu Gly Gly Phe Tyr Phe Tyr Ala Met Asp Tyr Trp Gly Gln
            100                 105                 110

Gly Thr Ser Val Thr Val Ser Ser
            115                 120

<210> SEQ ID NO 5
<211> LENGTH: 120
<212> TYPE: PRT
<213> ORGANISM: Mus musculus

<400> SEQUENCE: 5

Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asp Tyr
                 20                  25                  30

Ser Ile His Trp Val Lys Gln Ala Pro Gly Lys Gly Leu Lys Trp Met
             35                  40                  45

Gly Trp Ile Asn Thr Glu Thr Gly Ala Pro Thr Phe Ala Asp Asp Phe
 50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                 85                  90                  95

Ala Lys Glu Gly Gly Phe Tyr Phe Tyr Ala Met Asp Tyr Trp Gly Gln
            100                 105                 110

Gly Thr Ser Leu Thr Val Ser Ser
            115                 120

<210> SEQ ID NO 6
<211> LENGTH: 120
<212> TYPE: PRT
<213> ORGANISM: Mus musculus

<400> SEQUENCE: 6

Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asp Tyr
                 20                  25                  30

Ser Ile His Trp Val Lys Gln Ala Pro Gly Lys Gly Leu Lys Trp Met
             35                  40                  45

Ala Trp Ile Asn Thr Glu Thr Gly Asp Pro Thr Tyr Glu Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ser Lys Glu Gly Gly Phe Tyr Phe Tyr Ala Met Asp Tyr Trp Gly Gln
            100                 105                 110

Gly Thr Ser Val Thr Val Ser Ser
            115                 120
```

```
<210> SEQ ID NO 7
<211> LENGTH: 112
<212> TYPE: PRT
<213> ORGANISM: Mus musculus

<400> SEQUENCE: 7

Asp Ile Val Met Ser Gln Ser Pro Ser Ser Arg Ala Val Ser Ala Gly
1               5                   10                  15

Glu Lys Val Thr Met Ser Cys Lys Ser Gln Ser Leu Leu Ser Ser
            20                  25                  30

Arg Thr Arg Lys Asn Tyr Leu Ala Trp Tyr Gln Gln Lys Pro Gly Gln
        35                  40                  45

Ala Pro Lys Met Leu Ile Ser Trp Ala Ser Thr Arg Glu Phe Gly Val
    50                  55                  60

Pro Asp Arg Phe Thr Gly Ser Gly Phe Gly Thr Asp Phe Thr Leu Thr
65                  70                  75                  80

Ile Ser Ser Val Gln Gly Glu Asp Leu Ala Val Tyr Tyr Cys Lys Gln
                85                  90                  95

Ser Tyr Asn Phe Arg Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Mus musculus

<400> SEQUENCE: 8

Asp Ile Val Met Ser Gln Ser Pro Ser Ser Leu Ala Val Ser Ala Gly
1               5                   10                  15

Glu Lys Val Thr Met Ser Cys Lys Ser Gln Ser Leu Leu Ser Ser
            20                  25                  30

Arg Thr Arg Lys Asn Tyr Leu Ala Trp Tyr Gln Gln Lys Pro Gly Gln
        35                  40                  45

Ala Pro Lys Leu Leu Ile Ser Trp Ala Ser Thr Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 9
<211> LENGTH: 112
<212> TYPE: PRT
<213> ORGANISM: Mus musculus

<400> SEQUENCE: 9

Asp Ile Val Met Ser Gln Ser Pro Ser Ser Leu Ala Val Ser Ala Gly
1               5                   10                  15

Glu Lys Val Thr Met Asn Cys Lys Ser Gln Ser Leu Leu Ser Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Lys Gln
                85                  90                  95

Ser Tyr Asn Phe Arg Thr Phe Gly Gly Gly Thr Lys Leu Glu Ile Lys
            100                 105                 110
```

<210> SEQ ID NO 10
<211> LENGTH: 112
<212> TYPE: PRT
<213> ORGANISM: Mus musculus

<400> SEQUENCE: 10

```
Asp Ile Val Met Ser Gln Ser Pro Ser Ser Leu Ala Val Ser Thr Gly
1               5                   10                  15

Glu Lys Val Thr Met Ser Cys Lys Ser Gln Ser Leu Leu Ser Ser
                20                  25                  30

Arg Thr Arg Lys Asn Tyr Leu Ala Trp Tyr Gln Gln Lys Pro Gly Gln
            35                  40                  45

Ala Pro Lys Leu Leu Ile Ser Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Asn Leu Arg Thr Phe Gly Gly Gly Thr Lys Leu Glu Ile Lys
            100                 105                 110
```

<210> SEQ ID NO 11
<211> LENGTH: 112
<212> TYPE: PRT
<213> ORGANISM: Mus musculus

<400> SEQUENCE: 11

```
Asp Ile Val Met Ser Gln Ser Pro Ser Ser Leu Ala Val Ser Ala Gly
1               5                   10                  15

Glu Lys Val Thr Met Ser Cys Lys Ser Gln Ser Leu Leu Ser Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Lys Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110
```

<210> SEQ ID NO 12
<211> LENGTH: 7
<212> TYPE: PRT
<213> ORGANISM: Mus musculus

<400> SEQUENCE: 12

```
Gly Tyr Thr Phe Thr Asp Tyr
1               5
```

<210> SEQ ID NO 13
<211> LENGTH: 7

```
<212> TYPE: PRT
<213> ORGANISM: Mus musculus

<400> SEQUENCE: 13

Gly Tyr Ala Phe Thr Asp Tyr
1               5

<210> SEQ ID NO 14
<211> LENGTH: 5
<212> TYPE: PRT
<213> ORGANISM: Mus musculus

<400> SEQUENCE: 14

Asp Tyr Ser Ile His
1               5

<210> SEQ ID NO 15
<211> LENGTH: 6
<212> TYPE: PRT
<213> ORGANISM: Mus musculus

<400> SEQUENCE: 15

Asn Thr Glu Thr Gly Ala
1               5

<210> SEQ ID NO 16
<211> LENGTH: 6
<212> TYPE: PRT
<213> ORGANISM: Mus musculus

<400> SEQUENCE: 16

Asn Thr Glu Thr Ala Lys
1               5

<210> SEQ ID NO 17
<211> LENGTH: 6
<212> TYPE: PRT
<213> ORGANISM: Mus musculus

<400> SEQUENCE: 17

Asn Thr Glu Thr Gly Asp
1               5

<210> SEQ ID NO 18
<211> LENGTH: 17
<212> TYPE: PRT
<213> ORGANISM: Mus musculus

<400> SEQUENCE: 18

Trp Ile Asn Thr Glu Thr Gly Ala Pro Thr Phe Ala Asp Asp Phe Lys
1               5                   10                  15

Gly

<210> SEQ ID NO 19
<211> LENGTH: 17
<212> TYPE: PRT
<213> ORGANISM: Mus musculus

<400> SEQUENCE: 19

Trp Ile Asn Thr Glu Thr Ala Lys Pro Ala Phe Gly Asp Asp Phe Lys
1               5                   10                  15

Gly
```

```
<210> SEQ ID NO 20
<211> LENGTH: 17
<212> TYPE: PRT
<213> ORGANISM: Mus musculus

<400> SEQUENCE: 20

Trp Ile Asn Thr Glu Thr Gly Asp Pro Thr Tyr Glu Asp Asp Phe Lys
1               5                   10                  15

Gly

<210> SEQ ID NO 21
<211> LENGTH: 11
<212> TYPE: PRT
<213> ORGANISM: Mus musculus

<400> SEQUENCE: 21

Glu Gly Gly Phe Tyr Phe Tyr Ala Met Asp Tyr
1               5                   10

<210> SEQ ID NO 22
<211> LENGTH: 17
<212> TYPE: PRT
<213> ORGANISM: Mus musculus

<400> SEQUENCE: 22

Lys Ser Ser Gln Ser Leu Leu Ser Ser Arg Thr Arg Lys Asn Tyr Leu
1               5                   10                  15

Ala

<210> SEQ ID NO 23
<211> LENGTH: 7
<212> TYPE: PRT
<213> ORGANISM: Mus musculus

<400> SEQUENCE: 23

Trp Ala Ser Thr Arg Glu Phe
1               5

<210> SEQ ID NO 24
<211> LENGTH: 7
<212> TYPE: PRT
<213> ORGANISM: Mus musculus

<400> SEQUENCE: 24

Trp Ala Ser Thr Arg Glu Ser
1               5

<210> SEQ ID NO 25
<211> LENGTH: 7
<212> TYPE: PRT
<213> ORGANISM: Mus musculus

<400> SEQUENCE: 25

Trp Ala Ser Thr Arg Asp Ser
1               5

<210> SEQ ID NO 26
<211> LENGTH: 8
<212> TYPE: PRT
<213> ORGANISM: Mus musculus

<400> SEQUENCE: 26

Lys Gln Ser Tyr Asn Phe Arg Thr
1               5
```

<210> SEQ ID NO 27
<211> LENGTH: 8
<212> TYPE: PRT
<213> ORGANISM: Mus musculus

<400> SEQUENCE: 27

Lys Gln Ser Tyr Asn Leu Arg Thr
1               5

<210> SEQ ID NO 28
<211> LENGTH: 8
<212> TYPE: PRT
<213> ORGANISM: Mus musculus

<400> SEQUENCE: 28

Lys Gln Ser Phe Asn Leu Arg Thr
1               5

<210> SEQ ID NO 29
<211> LENGTH: 360
<212> TYPE: DNA
<213> ORGANISM: Mus musculus

<400> SEQUENCE: 29

```
cagatccagt tggtgcagtc tggacctgag ttgaagaagc tggagagac agtcaagatc      60
tcctgcaagg cttctggtta taccttcaca gactattcaa tacactgggt gaagcaggct    120
ccaggagagg gtttaaagtg gatggcctgg ataaacactg agactggtgc gccaacattt    180
gcagatgact tcaagggacg gttagccctc tctttggaga cttctgccaa cactgcctat    240
ttgcagatca caaccctcaa acatgaagac acggctacat atttctgtgc taaagaaggt    300
ggtttctact tttatgctat ggactactgg ggtcaaggaa cctcagtcac cgtctcctca    360
```

<210> SEQ ID NO 30
<211> LENGTH: 336
<212> TYPE: DNA
<213> ORGANISM: Mus musculus

<400> SEQUENCE: 30

```
gacattgtga tgtcacagtc tccatcctcc cgggctgtgt cagcaggaga gaaggtcact     60
atgagctgca atccagtca gagtctgctc agcagtcgaa cccgaaagaa ctacttggct    120
tggtaccaac agaaaccagg gcaggctcct aaaatgctga tttcctgggc atccactagg    180
gaatttgggg tccctgatcg cttcacaggc agtggatttg gcacagattt cactctcacc    240
attagcagtg tgcagggtga ggacctggca gtttattact gcaaacaatc ttataatttt    300
cggacgttcg gtggaggcac caagctggaa atcaaa                              336
```

<210> SEQ ID NO 31
<211> LENGTH: 360
<212> TYPE: DNA
<213> ORGANISM: Mus musculus

<400> SEQUENCE: 31

```
cagatccagt tggtgcagtc tggacctgag ttgaagaagc tggagagac agtcaagatc      60
tcctgcaagg cttctggtta taccttcaca gactattcaa tacactgggt gaagcaggct    120
ccaggagagg gtttaaagtg gatggcctgg ataaacactg agactggtgc gccaacattt    180
gcagatgact tcaagggacg gttagccctc tctttggaga cctctgccaa cactgcctat    240
```

```
ttgcagatca acaacctcaa acatgaagac acggcaacat atttctgtgc taaagaaggt    300
ggtttctact tttatgctat ggactattgg ggtcaaggaa cctcagtcac cgtctcttca    360
```

<210> SEQ ID NO 32
<211> LENGTH: 360
<212> TYPE: DNA
<213> ORGANISM: Mus musculus

<400> SEQUENCE: 32

```
cagatccagt tggtgcagtc tggacctgag ctgaagaagc tggagagac agtcaagatc     60 tcctgcaagg cttctggtta tgccttcaca gactattcaa tacactggat gaagcaggct    120
ccaggagagg gtctacagtg gatgggctgg ataaacactg agactgctaa gccagcattt    180
ggagatgact tcaagggacg gtttgccttt tctttggaaa cctctgccaa cactgcccat    240
ttgcacatca acaacctcag aactgaagac acggctacat atttctgtgc taaagaaggt    300
ggtttctact tttatgctat ggactattgg ggtcaaggaa cctcagtcac cgtctcctca    360
```

<210> SEQ ID NO 33
<211> LENGTH: 360
<212> TYPE: DNA
<213> ORGANISM: Mus musculus

<400> SEQUENCE: 33

```
cagatccagt tggtgcagtc tggacctgag ttgaagaagc tggagagac agtcaagatc     60 tcctgcaagg cttctggtta taccttcaca gactattcaa tacactgggt gaagcaggct    120
ccaggaaagg gtttaaagtg gatgggctgg ataaacactg agactggtgc gccaacattt    180
gcagatgact tcaagggacg gtttgccttc tctttggaaa cctctgccag cactgccttt    240
ttgcagatca acaacctcaa aaatgaagac acggctacat atttctgtgc taaggaaggt    300
ggtttctact tttacgctat ggactactgg ggtcaaggaa cctcgctcac cgtctcctca    360
```

<210> SEQ ID NO 34
<211> LENGTH: 360
<212> TYPE: DNA
<213> ORGANISM: Mus musculus

<400> SEQUENCE: 34

```
cagatccagt tggtgcagtc tggacctgag ctgaagaagc tggagagac agtcaagatc     60 tcctgcaagg cctctggtta taccttcaca gactactcaa tacactgggt gaagcaggct    120
ccaggaaagg gtttaaagtg gatggcctgg ataaacactg agactggtga cccaacatat    180
gaagatgact tcaagggacg gtttgccttc tctttggaaa cctctgccag cactgcctat    240
ttgcagatca acaacctcaa aaatgaggac acggctacat atttctgttc taaagaaggt    300
ggtttctact tttatgctat ggactactgg ggtcaaggaa cctcagtcac cgtctcctca    360
```

<210> SEQ ID NO 35
<211> LENGTH: 336
<212> TYPE: DNA
<213> ORGANISM: Mus musculus

<400> SEQUENCE: 35

```
gacattgtga tgtcacagtc tccatcctcc ctggctgtgt cagcaggaga gaaggtcact     60
atgagctgca gtccagtca gagtctgctc agcagtcgaa cccgaaagaa ctacttggct    120
tggtaccaac agaaaccagg gcaggctcct aaactgctga tctcctgggc atccactagg    180
gaatctgggg tccctgatcg cttcacaggc agtggatctg ggacagaatt cactctcacc    240
```

```
atcagcagtg tgcaggctga ggacctggca gtttattact gcaaacaatc ttataatctt    300
cggacgttcg gtggaggcac caagctggaa atcaaa                              336

<210> SEQ ID NO 36
<211> LENGTH: 336
<212> TYPE: DNA
<213> ORGANISM: Mus musculus

<400> SEQUENCE: 36
gacattgtga tgtcacagtc tccatcctcc ctggctgtgt cagcaggaga gaaggtcact     60
atgaactgca atccagtca gagtctgctc agcagtagaa cccgaaagaa ctacttggct    120
tggtaccagc agaaaccagg gcagtctcct aaactgctga tctactgggc ttccactagg    180
gactctgggg tccctgatcg cttcacaggc agtggatctg ggacagattt cactctcacc    240
atcagcagtg tgcaggcaga ggacctggca gtttattact gcaagcaatc ttataatttt    300
cggacgttcg gtggaggcac caagctggaa atcaaa                              336

<210> SEQ ID NO 37
<211> LENGTH: 336
<212> TYPE: PRT
<213> ORGANISM: Mus musculus

<400> SEQUENCE: 37

Gly Ala Cys Ala Thr Thr Gly Thr Gly Ala Thr Gly Thr Cys Ala Cys
1               5                   10                  15

Ala Gly Thr Cys Thr Cys Cys Ala Thr Cys Cys Thr Cys Cys Cys Thr
            20                  25                  30

Gly Gly Cys Thr Gly Thr Ala Thr Cys Ala Gly Cys Ala Gly Gly Ala
        35                  40                  45

Gly Ala Gly Ala Ala Gly Gly Thr Cys Ala Cys Thr Ala Thr Gly Ala
    50                  55                  60

Gly Cys Thr Gly Cys Ala Ala Thr Cys Cys Ala Gly Thr Cys Ala
65                  70                  75                  80

Gly Ala Gly Thr Cys Thr Gly Cys Thr Cys Ala Gly Cys Ala Gly Thr
                85                  90                  95

Cys Gly Ala Ala Cys Cys Cys Gly Ala Ala Gly Ala Ala Cys Thr
            100                 105                 110

Ala Cys Thr Thr Gly Gly Cys Thr Thr Gly Gly Thr Ala Cys Cys Ala
        115                 120                 125

Ala Cys Ala Gly Ala Ala Ala Cys Cys Ala Gly Gly Gly Cys Ala Gly
    130                 135                 140

Gly Cys Thr Cys Cys Thr Ala Ala Ala Cys Thr Gly Cys Thr Gly Ala
145                 150                 155                 160

Thr Cys Thr Ala Cys Thr Gly Gly Gly Cys Ala Thr Cys Cys Ala Cys
                165                 170                 175

Thr Ala Gly Gly Gly Ala Ala Cys Thr Gly Gly Gly Gly Thr Cys
            180                 185                 190

Cys Cys Thr Gly Ala Thr Cys Gly Cys Thr Thr Cys Ala Cys Ala Gly
        195                 200                 205

Gly Cys Ala Gly Thr Gly Gly Ala Thr Cys Thr Gly Gly Gly Ala Cys
    210                 215                 220

Ala Gly Ala Thr Thr Thr Cys Ala Cys Thr Cys Thr Cys Ala Cys Cys
225                 230                 235                 240

Ala Thr Cys Ala Gly Cys Ala Gly Thr Gly Thr Gly Cys Ala Gly Gly
```

```
                       245                 250                 255
Cys Thr Gly Ala Ala Gly Ala Cys Cys Thr Gly Gly Cys Ala Gly Thr
                260                 265                 270

Thr Thr Ala Thr Thr Ala Cys Thr Gly Cys Ala Ala Ala Cys Ala Ala
            275                 280                 285

Thr Cys Thr Thr Thr Ala Ala Thr Cys Thr Thr Cys Gly Gly Ala
        290                 295                 300

Cys Gly Thr Thr Cys Gly Gly Thr Gly Gly Ala Gly Gly Cys Ala Cys
305                 310                 315                 320

Cys Ala Ala Ala Cys Thr Gly Gly Ala Ala Ala Thr Cys Ala Ala Ala
                325                 330                 335

<210> SEQ ID NO 38
<211> LENGTH: 336
<212> TYPE: DNA
<213> ORGANISM: Mus musculus

<400> SEQUENCE: 38
gacattgtga tgtcacagtc tccatcctcc ctggctgtgt cagcaggaga gaaggtcact      60
atgagctgca aatccagtca gagtctgctc agcagtagaa cccgaaagaa ctacttggct     120
tggtaccagc agaaaccagg gcagtctcct aaactgctga ttaaatgggc atccactagg     180
gaatctgggg tccctgatcg cttcacaggc agtggatctg ggacagattt cactctcacc     240
atcagcagtg tgcaggctga agacctggca gtttattact gcaagcaatc ttataatctt     300
cggacgttcg gtggaggcac caagctggaa atcaaa                               336
```

ANTI-TALEN ANTIBODIES AND USES THEREOF

CROSS REFERENCE

The present application claims the benefit of priority to U.S. Provisional Application No. 62/861,214, filed on Jun. 13, 2019, the content of which is hereby incorporated by reference in its entirety.

SEQUENCE LISTING

This application contains a Sequence Listing which has been submitted electronically in ASCII format and is hereby incorporated by reference in its entirety. Said ASCII copy, created on Jun. 12, 2020, is named AT-021_02_SL_ST25.txt and is 26,590 bytes in size.

TECHNICAL FIELD

The present disclosure relates to antigen binding molecules, including, but not limited to, antibodies, which specifically bind gene editing proteins (e.g., TALEN proteins comprising a FokI, also referred to as Fok-1 or Fok1, catalytic domain) and polynucleotides encoding the same, and methods of use.

BACKGROUND

Genome editing tools such as Transcription activator-like effector nucleases (TALEN®), Zinc-finger nucleases (ZFNs), and RNA-guided FokI Nucleases (RFNs) are powerful tools that enable the precise revision, insertion or deletion of genes. TALENs, ZFNs, and RFNs can bind to and cleave at targeted sites in a genome. The resulting cleaved DNA is repaired via the endogenous cell DNA repair mechanism of non-homologous end joining (NHEJ), or via homology-directed repair (HDR) when a repair template is provided. TALENs use a TAL effector DNA-binding domain fused to a DNA cleavage domain (e.g., FokI). ZFNs are composed of a restriction endonuclease cleavage or catalytic domain, such as FokI, linked to engineered $Cys_2His_2$ zinc-finger, DNA-binding polypeptides. RFNs are composed of a FokI nuclease fused to catalytically inactive form of Cas9. For efficient genome editing in mammals (e.g., humans, dogs, cattle, non-human primates, etc.), it is envisioned that TALENs, ZFNs and RFNs will be expressed at high level. Due to the risk of sustained nuclease activity and off-target effects, as well as potential immunogenicity, there is a need in the art for antibodies that recognize genome editing tools (e.g., anti-TALEN and/or anti-FokI antibodies) capable of binding nuclease proteins in order to evaluate the safety and efficacy of various gene editing therapies.

SUMMARY OF THE INVENTION

The present disclosure provides, among other things, antibodies for the detection of FokI catalytic domains and full-length TALEN proteins in a sample. As described herein, including in the Examples below, the present disclosure provides anti-TALEN antibodies which specifically bind TALEN and FokI proteins. In some embodiments anti-TALEN antibodies of the present disclosure can be used to evaluate gene editing therapies and processes.

In one aspect, the instant disclosure provides an anti-TALEN antibody comprising a variable heavy chain amino acid sequence that is at least 85% identical to SEQ ID NO: 3 and a variable light chain amino acid sequence that is at least 85% identical to SEQ ID NO: 7. In one embodiment the anti-TALEN antibody is humanized. In various embodiments, the antibody is selected from the group consisting of an antibody, an scFv, a Fab, a Fab', a Fv, a F(ab')$_2$, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody an IgG2 antibody having at least one mutation in the hinge region, an IgG3 antibody, an IgG3 antibody having at least one mutation in the hinge region, an IgG4 antibody, an IgG4 antibody having at least one mutation in the hinge region, an antibody comprising at least one non-naturally occurring amino acid, and any combination thereof.

In specific embodiments, the antibody comprises a variable heavy chain (HC) selected from the group consisting of SEQ ID NOs: 3-6, and in further embodiments the anti-TALEN antibody comprises a heavy chain CDR1 selected from the group consisting of SEQ ID NOs: 12-14, and/or a heavy chain CDR2 selected from the group consisting of SEQ ID NOs: 15-20, and/or a heavy chain CDR3 comprising SEQ ID NO: 21. In specific embodiments, an anti-TALEN antibody comprises a heavy chain CDR1, a heavy chain CDR2, and a heavy chain CDR3, each CDR comprising an amino acid sequence shown in Table 1c. Also provided is an anti-TALEN antibody comprising a VH amino acid sequence that is at least about 90%, at least about 95%, at least about 96%, at least about 97%, at least about 98%, at least about 99%, or about 100% identical to a VH of an antigen binding molecule provided herein.

In other embodiments an anti-TALEN antibody comprises a light chain variable region (VL) sequence selected from the group consisting of SEQ ID NOs: 7-11. In specific embodiments, an anti-TALEN antibody comprises a light chain CDR1 comprising SEQ ID NO: 22, and/or a light chain CDR2 selected from the group consisting of SEQ ID NO: 23-25, and/or a light chain CDR3 selected from the group consisting of SEQ ID NOs: 26-28. Further provided is an anti-TALEN antibody wherein the light chain comprises a light chain CDR1, a light chain CDR2 and a light chain CDR3, each CDR comprising an amino acid sequence in Table 1d. Also provided is an anti-TALEN antibody, comprising a VL amino acid sequence that is at least about 90%, at least about 95%, at least about 96%, at least about 97%, at least about 98%, at least about 99%, or about 100% identical to a VL of an antigen binding molecule provided herein.

In another embodiment, provided herein is an anti-TALEN antibody, comprising (a) a VH CDR1 comprising the amino acid sequence of SEQ ID NO:12; (b) a VH CDR2 comprising the amino acid sequence of SEQ ID NO: 15; (c) a VH CDR3 comprising the amino acid sequence of SEQ ID NO: 21; (d) a VL CDR1 comprising the amino acid sequence of SEQ ID NO: 22; (e) a VL CDR2 comprising the amino acid sequence of SEQ ID NO: 23; and (f) a VL CDR3 comprising the amino acid sequence of SEQ ID NO: 26 and in a further embodiment, an anti-TALEN antibody comprises (a) a VH comprising the amino acid sequence of SEQ ID NO: 3; and (b) a VL comprising the amino acid sequence of SEQ ID NO: 7.

In another embodiment provided herein is an anti-TALEN antibody, comprising (a) a VH CDR1 comprising the amino acid sequence of SEQ ID NO: 12; (b) a VH CDR2 comprising the amino acid sequence of SEQ ID NO: 16; (c) a VH CDR3 comprising the amino acid sequence of SEQ ID NO: 21; (d) a VL CDR1 comprising the amino acid sequence of SEQ ID NO: 22; (e) a VL CDR2 comprising the amino acid sequence of SEQ ID NO: 24; and (f) a VL CDR3 comprising the amino acid sequence of SEQ ID NO: 27, and in a further embodiment an anti-TALEN antibody comprises (a) a VH comprising the amino acid sequence of SEQ ID NO: 3; and (b) a VL comprising the amino acid sequence of SEQ ID NO: 8.

In a further embodiment, provided herein is an anti-TALEN antibody comprising (a) a VH CDR1 comprising the amino acid sequence of SEQ ID NO: 13; (b) a VH CDR2 comprising the amino acid sequence of SEQ ID NO: 16; (c) a VH CDR3 comprising the amino acid sequence of SEQ ID NO: 21; (d) a VL CDR1 comprising the amino acid sequence of SEQ ID NO: 22; (e) a VL CDR2 comprising the amino acid sequence of SEQ ID NO: 25; and (f) a VL CDR3 comprising the amino acid sequence of SEQ ID NO: 26, and in a further embodiment the anti-TALEN antibody comprises (a) a VH comprising the amino acid sequence of SEQ ID NO: 4; and (b) a VL comprising the amino acid sequence of SEQ ID NO: 9.

In still a further embodiment, provided herein is an anti-TALEN antibody comprising (a) a VH CDR1 comprising the amino acid sequence of SEQ ID NO: 12; (b) a VH CDR2 comprising the amino acid sequence of SEQ ID NO: 15; (c) a VH CDR3 comprising the amino acid sequence of SEQ ID NO: 21; (d) a VL CDR1 comprising the amino acid sequence of SEQ ID NO: 22; (e) a VL CDR2 comprising the amino acid sequence of SEQ ID NO: 24; and (f) a VL CDR3 comprising the amino acid sequence of SEQ ID NO: 28, and in a further embodiment the anti-TALEN antibody comprises (a) a VH comprising the amino acid sequence of SEQ ID NO: 5; and (b) a VL comprising the amino acid sequence of SEQ ID NO: 10.

Also provided is an anti-TALEN antibody, comprising (a) a VH CDR1 comprising the amino acid sequence of SEQ ID NO: 12; (b) a VH CDR2 comprising the amino acid sequence of SEQ ID NO: 17; (c) a VH CDR3 comprising the amino acid sequence of SEQ ID NO: 21; (d) a VL CDR1 comprising the amino acid sequence of SEQ ID NO: 22; (e) a VL CDR2 comprising the amino acid sequence of SEQ ID NO: 24; and (f) a VL CDR3 comprising the amino acid sequence of SEQ ID NO: 27, and in a further embodiment the anti-TALEN antibody of claim 24, comprising (a) a VH comprising the amino acid sequence of SEQ ID NO: 6; and (b) a VL comprising the amino acid sequence of SEQ ID NO: 11.

In various embodiments the anti-TALEN antibody further comprises a detectable label, and in some embodiments the detectable label is selected from the group consisting of a fluorescent label, a photochromic compound, a proteinaceous fluorescent label, a magnetic label, a radiolabel, and a hapten. When the detectable label is a fluorescent label, the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, *Lucifer* Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry. In specific embodiments the fluorescent label is R-Phycoerythrin (PE) or Allophycocyanin (APC)

Also provided is a composition comprising an anti-TALEN antibody provided herein and an acceptable carrier or vehicle, e.g., a pharmaceutically acceptable carrier or vehicle.

Polynucleotides encoding the heavy chain of an anti-TALEN antibody disclosed herein are also provided. Polynucleotide encoding the light chain of an anti-TALEN antibody disclosed herein are also provided. Vectors comprising one or both of the heavy and light chain encoding polynucleotides are also provided. Further, a cell comprising one or both of the vectors is provided, and the cell can comprise a cell selected from the group consisting of a CHO cell, a Sp2/0 cell, a rabbit cell and an *E. coli* cell. A method of making an anti-TALEN antibody disclosed herein is provided and comprises incubating a cell comprising one or both of the vectors described above under suitable conditions.

In yet a further embodiment a method of determining the presence or absence of a TALEN protein in a sample is provided and in one embodiment comprises contacting the sample with an anti-TALEN antibody conjugated to a detectable label and determining the presence or absence of the TALEN protein in the sample; in some embodiments the anti-TALEN antibody comprises an antibody provided herein, or a humanized form thereof. Additionally, the sample can be a tissue sample, a blood sample, a formalin-fixed sample, a tissue grown ex vivo or cell culture media.

Various aspects of the present disclosure are described in detail in the following sections. The use of sections is not meant to limit the present disclosure. Each section can apply to any aspect of the present disclosure. In this application, the use of "or" means "and/or" unless stated otherwise. All references cited herein are incorporated by reference in their entirety. Unless otherwise defined, all technical and scientific terms used herein have the same meaning as commonly understood by one of ordinary skill in the art to which the present disclosure belongs.

BRIEF DESCRIPTION OF THE DRAWINGS

The drawings provided in the present disclosure are for illustration purposes only and not for limitation.

FIG. 1 depicts a Western blot analysis of hybridoma supernatants from fusion #2299 (Numbers 13-16 noted in the FIGURE) and #2296 (Numbers 3, 6, 7, 8, and 11 noted in the FIGURE).

DEFINITIONS

Unless defined otherwise, all technical and scientific terms used herein have the same meaning as commonly understood by one of ordinary skill in the art (e.g., in the arts of genetic engineering, cell culture, molecular genetics, nucleic acid chemistry and biochemistry).

In order for the present disclosure to be more readily understood, certain terms are first defined below. Additional definitions for the following terms and other terms are set forth throughout the present disclosure.

Affinity: As is known in the art, "affinity" refers to a measure of the tightness that a particular ligand binds to its partner. Affinities can be measured in different ways. In some embodiments, affinity is measured by a quantitative assay. In some embodiments, binding partner concentration and/or ligand concentration can be varied. In some such embodiments, affinity can be compared to a reference under comparable conditions (e.g., concentrations).

Amino acid: in its broadest sense, refers to any compound and/or substance that can be incorporated into a polypeptide chain, e.g., through formation of one or more peptide bonds. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. The term "standard amino acid" refers to any of the twenty standard L-amino acids commonly found in naturally occurring peptides. The term "nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid can be modified by methylation, amidation, acetylation, and/or substitution as compared with the general structure. As will be clear from context, in some embodiments, the term "amino acid" is used to refer to a free amino acid; in some embodiments it is used to refer to an amino acid residue of a polypeptide.

Antibody: As used herein, the term "antibody" refers to a species of antigen binding proteins comprising a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long), an amino-terminal variable (VH) domain (located at the tips of the Y structure), followed by three constant domains: CH1, CH2, and the carboxy-terminal CH3 (located at the base of the Y's stem). A short region, commonly referred to as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. In some embodiments, an antibody is polyclonal; in some embodiments, an antibody is monoclonal.

Binding: It will be understood that the term "binding", as used herein, typically refers to a non-covalent association between or among two or more entities. "Direct" binding involves physical contact between entities or moieties; "indirect" binding involves physical interaction by way of physical contact with one or more intermediate entities.

Chromosome: As used herein, the term "chromosome" refers to a linear molecule of DNA with associated proteins in the nucleus of eukaryotic cells that carries the genes and functions in the transmission of hereditary information.

Corresponding to: as used herein designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Detection moiety: The term "detection moiety" as used herein refers to any element, molecule, functional group, compound, fragment or moiety that is detectable. In some embodiments, a detection moiety is provided or utilized alone. In some embodiments, a detection moiety is provided and/or utilized in association with (e.g., joined to) another agent. Examples of detection moieties include, but are not limited to: various ligands, radionuclides (e.g., $^3H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (such as, for example fluorescein dyes, acridine dyes, SYBR dyes, rhodamine dyes, oxazine dyes, etc.), chemiluminescent agents (such as, for example, acridinum esters, stabilized dioxetanes, and the like), electrochemiluminescent agents (such as, for example, Sulfo Tags), bioluminescent agents (such as, for example, luciferin), spectrally resolvable inorganic fluorescent semiconductors nanocrystals (i.e., quantum dots), metal nanoparticles (e.g., gold, silver, copper, platinum, etc.), nanoclusters, paramagnetic metal ions, enzymes (such as, for example, horseradish peroxidase, alkaline phosphatase, etc.), colorimetric labels (such as, for example, dyes, colloidal gold, and the like), biotin, digoxigenin, haptens, and proteins for which antisera or monoclonal antibodies are available.

Engineered: In general, the term "engineered" refers to the aspect of having been manipulated by the hand of man. For example, a polynucleotide is considered to be "engineered" when two or more sequences that are not linked together in that order in nature are manipulated by the hand of man to be directly linked to one another in the engineered polynucleotide. For example, in some embodiments of the present disclosure, an engineered polynucleotide can comprise a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or by a deletion mutation, or by mating protocols). As is common practice and is understood by those in the art, progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

FokI: As used herein, the term "FokI" (alternatively referred to as Fok1 or Fok-1) refers to a bacterial type IIS restriction endonuclease that is naturally found in *Flavobacterium okeanokoites*. Natural FokI comprises of an N-terminal DNA-binding domain and a non-specific DNA cleavage domain at the C-terminus. The FokI DNA cleavage domain can function independently of the DNA binding domain. As used herein, FokI refers to a protein or a nucleic acid encoding a protein that comprises the DNA cleavage domain (i.e., the nuclease domain) of FokI. FokI can refer to the entire FokI protein (SEQ ID NO: 2) or just the catalytic nuclease domain (SEQ ID NO: 1). The term "FokI" refers to all fragments and variants of FokI including mutants, derivatives, analogs, truncations, fusion constructs, and multimers of FokI, including FokI dimers. In some embodiments, FokI is recombinantly produced. In some embodiments, a FokI polypeptide is conjugated to or tagged with an additional moiety, such as a binding moiety and/or a detection moiety. As will be clear from context, in some embodiments, the term "FokI" is used to refer to the FokI polypeptide or fragments or variants thereof; in some embodiments "FokI" is used to refer to nucleic acids encoding a FokI polypeptide and fragments and variants thereof.

Fragment: A "fragment" of a biological molecule as described herein has a structure that includes a discrete portion of the whole but lacks one or more moieties found in the whole (e.g., a polypeptide lacking one or more amino acids). In some embodiments, a fragment consists of such a discrete portion. In some embodiments, a fragment consists of or comprises a characteristic structural element or moiety found in the whole (e.g. a polypeptide domain). In some embodiments, the biological molecule is a polymer (e.g. a nucleic acid polymer or a polypeptide). In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. In some embodiments, the whole biological molecule can be referred to as the "parent" of the whole.

Fusion: A "fusion molecule" is a molecule in which two or more subunit molecules are linked, preferably covalently. The subunit molecules can be the same chemical type of molecule or can be different chemical types of molecules. Examples fusions of the same chemical type of molecule include, but are not limited to, fusion proteins (for example, a fusion between a Zinc Finger Protein or TALEN DNA-binding domain to a FokI cleavage domain) and fusion nucleic acids (for example, a nucleic acid encoding the fusion protein described supra). Examples fusions of different chemical types of molecule include, but are not limited to, nucleic acid-polypeptide fusions (for example, a fusion between an RNA molecule and a FokI cleavage domain).

Gene: As used herein, the term "gene" refers to a DNA sequence that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene can include both coding (e.g., exonic) and non-coding (e.g., intronic) sequence. In some embodiments, a gene can include one or more regulatory elements that, for example, can control or impact one or more aspects of gene expression (e.g., cell-type-specific expression, inducible expression, etc).

Gene or Cell therapy: As used herein, the term "gene or cell therapy" refers to insertion or deletion of specific genomic DNA sequences to treat or prevent a disorder or condition for which such therapy is sought. In some embodiments, the insertion or deletion of genomic DNA sequences occurs in specific cells (i.e. target cells). Target cells can be from a mammal and/or can be cells in a mammalian subject. Mammals include but are not limited to humans, dogs, cats, cows, sheep, pigs, llamas, non-human primates, etc. In some embodiments, heterologous DNA is transferred to target cells. The heterologous DNA can be introduced into the selected target cells in a manner such that the heterologous DNA is expressed, and a therapeutic product encoded thereby is produced. Additionally, or alternatively, the heterologous DNA can in some manner mediate expression of DNA that encodes the therapeutic product, or it can encode a product, such as a peptide or RNA that in some manner mediates, directly or indirectly, expression of a therapeutic product. Genetic or cell therapy can also be used to deliver nucleic acid encoding a gene product that replaces a defective gene or supplements a gene product produced by the mammal or the cell in which it is introduced. The heterologous DNA encoding the therapeutic product can be modified prior to introduction into the cells of the afflicted subject in order to enhance or otherwise alter the product or expression thereof. Genetic or cell therapy can also involve delivery of an inhibitor or repressor or other modulator of gene expression. Gene therapy can include in vivo or ex vivo techniques. In some embodiments, gene or cell therapy includes administering nucleic acids encoding Transcription activator-like effector nucleases (TALENs), Zinc-Finger Nucleases (ZFNs) or RNA-guided FokI nucleases (RFNs). In some embodiments, viral and non-viral based gene transfer methods can be used to introduce nucleic acids encoding TALENs, ZFNs or RFNs into mammalian cells or target tissues.

Such methods can be used to administer nucleic acids encoding TALENs, ZFNs or RFNs to cells in vitro. Non-viral vector delivery systems include DNA plasmids, naked nucleic acid, and nucleic acid complexed with a delivery vehicle such as poloxamers or liposomes. Viral vector delivery systems include DNA and RNA viruses, which have either episomal or integrated genomes after delivery to the cell. For a review of gene therapy procedures, see, e.g., Anderson, *Science* 256:808-813 (1992); Miller, *Nature* 357: 455-460 (1992); Feuerbach et al., *Kidney International* 49:1791-1794 (1996); Urnov et al., *Nature Reviews Genetics* 11, 636-646 (2010); and Collins et al., *Proceedings Biologicial Sciences/The Royal Society,* 282(1821):pii 20143003 (2015).

Genome: As used herein, the term "genome" refers to the total genetic information carried by an individual organism or cell, represented by the complete DNA sequences of its chromosomes.

High affinity binding: The term "high affinity binding", as used herein refers to a high degree of tightness with which a particular ligand binds to its partner. Affinities can be measured by any available method, including those known in the art. In some embodiments, binding is considered to be high affinity if the $K_d$ is about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays. In some embodiments, binding is considered to be high affinity if the affinity is stronger (e.g., the $K_d$ is lower) for a polypeptide of interest than for a selected reference polypeptide. In some embodiments, binding is considered to be high affinity if the ratio of the $K_d$ for a polypeptide of interest to the $K_d$ for a selected reference polypeptide is 1:1 or less (e.g., 0.9:1, 0.8:1, 0.7:1, 0.6:1, 0.5:1.0.4:1, 0.3:1, 0.2:1, 0.1:1, 0.05:1, 0.01:1, or less). In some embodiments, binding is considered to be high affinity if the $K_d$ for a polypeptide of interest is about 100% or less (e.g., about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1% or less) of the $K_d$ for a selected reference polypeptide.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98%, or 99% similar.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term can be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities can be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance can still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques can be considered to be an "isolated" polypeptide to the extent that it has been separated from other components a) with which it is associated in nature; and/or b) with which it was associated when initially produced.

Linker: as used herein, is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 can be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) *Proc. Natl. Acad. Sci. USA* 90:6444-6448; Poljak, R. J., et al. (1994) *Structure* 2: 1 121-1123).

Nucleic acid: as used herein, in its broadest sense, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Physiological conditions: as used herein, has its art-understood meaning referencing conditions under which cells or organisms live and/or reproduce. In some embodiments, the term refers to conditions of the external or internal milieu that can occur in nature for an organism or cell system. In some embodiments, physiological conditions are those conditions present within the body of a human or non-human animal, especially those conditions present at and/or within a surgical site. Physiological conditions typically include, e.g., a temperature range of about 20-about 40° C., atmospheric pressure of about 1, pH of about 6-about 8, glucose concentration of about 1-about 20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides can contain L-amino acids, D-amino acids, or both and can contain any of a variety of amino acid modifications or analogs known in the art. Useful modifications include, e.g., terminal acetylation, amidation, methylation, etc. In some embodiments, proteins can comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" can be used interchangeably. If the discrete functional unit is comprised of more than one polypeptide that physically associate with one another, the term "protein" can be used to refer to the multiple polypeptides that are physically associated and function together as the discrete unit. In some embodiments, proteins can include moieties other than amino acids (e.g., glycoproteins, proteoglycans, etc.) and/or can be otherwise processed or modified. Those of ordinary skill in the art will appreciate that in some embodiments the term "protein" can refer to a complete polypeptide chain as produced by a cell (e.g., with or without a signal sequence), and/or to a form that is active within a cell (e.g., a truncated or complexed form). In some embodiments where a protein is comprised of multiple polypeptide chains, such chains can be covalently associated with one another, for example by one or more disulfide bonds, or can be associated by other means.

Reference: as used herein in a scientific context describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample can be or comprise bone marrow; blood; blood cells of any type (e.g., T cells); ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" can comprise, for example nucleic acids or proteins extracted from a sample or obtained by subjecting a primary sample to techniques such as amplification or reverse transcription of mRNA, isolation and/or purification of certain components, etc.

Specific binding: as used herein, refers to a binding agent's ability to discriminate between possible partners, in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is, will and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Variant As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule can have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (e.g., single vs double, E vs Z, etc.) within the core, a polypeptide can have a characteristic sequence element comprised of a plurality of amino acids having designated positions relative to one another in linear or three-dimensional space and/or contributing to a particular biological function, a nucleic acid can have a characteristic sequence element comprised of a plurality of nucleotide residues having designated positions relative to on another in linear or three-dimensional space. For example, a variant polypeptide can differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, 98% or 99%. Alternatively, or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% or 1% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. In some embodiments, the variant is engineered. In some embodiments the variant is naturally occurring. As will be understood by those of ordinary skill in the art, a plurality of variants of a particular polypeptide of interest can be found in nature.

Vector: as used herein, refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector (e.g., a lentiviral vector or a gamma retroviral vector), wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

Zinc finger protein: As used herein, the term "zinc finger protein" refers to a polypeptide that contains a "zinc finger domain" through which it is capable of binding to nucleic acids (e.g., DNA). The term "zinc finger domain" refers to an individual "finger", which comprises a ββα-fold stabilized by a zinc ion. Each zinc finger domain typically includes approximately 30 amino acids. Zinc finger domains are largely structurally independent and can retain their structure and function in different environments.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present disclosure are apparent in the detailed description that follows. It should be understood, however, that the detailed description, while indicating embodiments of the present disclosure, is given by way of illustration only, not limitation. Various changes and modifications within the scope of the present disclosure will become apparent to those skilled in the art from the detailed description.

DETAILED DESCRIPTION OF CERTAIN EMBODIMENTS

The present disclosure provides, antibodies that bind TALEN proteins and/or the FokI catalytic DNA cleavage domain and uses thereof.

As used herein, antibodies include, but are not limited to antibody binding regions that are immunologically functional fragments. The term "immunologically functional fragment" (or "fragment") of an antibody is a species of antibody comprising a portion (regardless of how that portion is obtained or synthesized) of an antibody that lacks at least some of the amino acids present in a full-length chain but which is still capable of specifically binding to a target antigen (e.g., binding to FokI and/or TALEN proteins). Such fragments are biologically active in that they bind to the target antigen and can compete with other antigen binding molecules, including intact antibodies, for binding to a given epitope. In some embodiments, the fragments are neutralizing fragments. In some embodiments, the fragments can block or reduce the activity of the target antigen (e.g., blocking effect). In some embodiments, the fragments can antagonize the activity the target antigen.

In specific embodiments, an anti-TALEN antibody of the instant disclosure is an antibody identified herein as clones 2299.2G3.C6, 2299.5D4.C8, 2299.6B3.B8.B6, 2299.6G5.C7, or 2299.7F11.B4. and each comprises the heavy and light chain amino acid, coding, variable, and CDR sequences, as provided and labeled herein. In some embodiments, the clones 2299.2G3.C6, 2299.5D4.C8, 2299.6B3.B8.B6, 2299.6G5.C7, or 2299.7F11.B4 specifically bind a molecule comprising a FokI catalytic domain.

Immunologically functional immunoglobulin fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multispecific antigen binding domains, and single-chain antibodies. These fragments can be derived from any mammalian source, including but not limited to human, mouse, rat, camelid or rabbit. As will be appreciated by one of skill in the art, an antigen binding molecule can include non-protein components.

The variable regions typically exhibit the same general structure of relatively conserved framework regions (FR) joined by the 3 hypervariable regions (CDRs). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3.

In some embodiments, anti-TALEN antibodies comprise one or more complementarity binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody of fragment thereof, including one or more of the complementarity determining regions (CDRs) thereof. In some embodiments, the antigen binding domain is a single chain variable fragment (scFv), comprising light chain CDRs CDR1, CDR2 and CDR3, and heavy chain CDRs CDR1, CDR2 and CDR3.

The assignment of amino acids to each of the framework, CDR, and variable domains is typically in accordance with numbering schemes of Kabat numbering (see, e.g., Kabat et al. in *Sequences of Proteins of Immunological Interest*, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) *J Mol Biol* 273: 927-948; Chothia et al., (1992) *J Mol Biol* 227: 799-817; Tramontano et al., (1990) *J Mol Biol* 215(1): 175-82; and U.S. Pat. No. 7,709,226), contact numbering, or the AbM scheme (Antibody Modeling program, Oxford Molecular).

Accordingly, in some embodiments, the CDRs of the anti-TALEN antibodies presented herein are numbered according to the Kabat numbering scheme. In other embodiments, the CDRs of the anti-TALEN antibodies presented herein are numbered according to the Chothia numbering scheme. In other embodiments, the CDRs of the anti-TALEN antibodies presented herein are numbered according to the contact numbering scheme. In other embodiments, the CDRs of the anti-TALEN antibodies presented herein are numbered according to the AbM numbering scheme.

Humanized antibodies of the anti-TALEN antibodies described herein can be prepared by known techniques. In some embodiments, a humanized monoclonal antibody comprises the variable domain of an anti-TALEN antibody (or all or part of the antigen binding site thereof) and a constant domain derived from a human antibody. Alternatively, a humanized antibody fragment can comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) *Nature* 332:323, Liu et al., (1987) *Proc. Nat. Acad. Sci. USA* 84:3439, Larrick et al., (1989) *Bio/Technology* 7:934, and Winter et al., (1993) *TIPS* 14:139. In some embodiments, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J.* 9:133-39; Tamura et al., (2000) *J. Immunol.* 164:1432-41; Zhang et al., (2005) *Mol. Immunol.* 42(12):1445-1451; Hwang et al., *Methods.* (2005) 36(1):35-42; Dall'Acqua et al., (2005) *Methods* 36(1):43-60; and Clark, (2000) *Immunology Today* 21(8):397-402.

Variants of the anti-TALEN antibodies are also within the scope of the disclosure, e.g., variable light and/or variable heavy chains that each have at least 70-80%, 80-85%, 85-90%, 90-95%, 95-97%, 97-99%, or above 99% identity to the amino acid sequences of the antigen binding domain sequences described herein. In some embodiments, the anti-idiotype antibody is at least about 75%, at least about 85%, at least about 85%, at least about 90%, at least about 95%, at least about 96%, at least about 97%, at least about 98%, at least about 99%, or 100% identical to a heavy chain variable region sequence provided in Table 1a and/or a light chain variable sequence provided in Table 1b.

In some instances, such molecules include at least one heavy chain and one light chain, whereas in other instances the variant forms contain two variable light chains and two variable heavy chains (or subparts thereof). A skilled artisan will be able to determine suitable variants of the anti-TALEN antibodies as set forth herein using well-known techniques. In certain embodiments, one skilled in the art can identify suitable areas of the molecule that can be changed without destroying antigen binding activity by targeting regions not believed to be important for activity.

An anti-TALEN antibody of the present disclosure can also be a fully human monoclonal antibody. Fully human monoclonal antibodies can be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

An anti-TALEN antibody that specifically binds to a TALEN protein and/or the FokI catalytic domain is said to be "selective" when it binds to one target more tightly than it binds to a second target. An anti-TALEN antibody that specifically binds to a TALEN protein and/or the FokI catalytic domain is said to "specifically bind" its target antigen (e.g., TALEN protein and/or the FokI catalytic domain) when the dissociation constant (Kd) is in the nanomolar range (e.g., ~1 nM). The antigen binding domain specifically binds antigen with "high affinity" when the Kd is 1-5 nM, and with "very high affinity" when the Kd is 0.1-0.5 nM. In one embodiment, the antigen binding domain has a Kd of ~1 nM. In one embodiment, the off-rate is $<1\times10^{-5}$. In other embodiments, the antigen binding domains will bind to TALEN proteins and molecules comprising FokI catalytic domain with a Kd of between about $1\times10^{-7}$ M and $1\times10^{-12}$ M, and in yet another embodiment the antigen binding domains will bind with a Kd between about $1\times10^{-5}$ and $1\times10^{-12}$.

As provided herein, the anti-TALEN antibodies of the present disclosure specifically bind TALEN proteins and/or the FokI nuclease domain (e.g., SEQ ID NO: 1). In certain embodiments, the anti-TALEN antibodies of the present disclosure bind TALEN proteins and/or the FokI catalytic domain with a KD of less than $1\times10^{-6}$ M, less than $1\times10^{-7}$ M, less than $1\times10^{-8}$ M, or less than $1\times10^{-9}$ M. In one particular embodiment, the anti-TALEN antibodies bind TALEN proteins and/or the FokI catalytic domain with a KD of less than $1\times10^{-7}$ M. In another embodiment, the anti-TALEN antibodies bind TALEN proteins and/or the FokI catalytic domain with a KD of less than $1\times10^{-8}$ M. In some embodiments, the anti-TALEN antibodies bind TALEN proteins and/or the FokI catalytic domain with a Kd of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. In certain embodiments, the Kd is calculated as the quotient of $K_{off}/K_{on}$, and the $K_{on}$ and $K_{off}$ are determined using a monovalent antibody, such as a Fab fragment, as measured by, e.g., Biacore® surface plasmon resonance technology. In other embodiments, the Kd is calculated as the quotient of $K_{off}/K_{on}$, and the $K_{on}$ and $K_{off}$ are determined using a bivalent antibody, such as a Fab fragment, as measured by, e.g., Biacore® surface plasmon resonance technology.

In some embodiments, the anti-TALEN antibodies bind TALEN proteins and/or the FokI catalytic domain with an association rate ($k_{on}$) of less than $1\times10^{-4}$ $M^{-1}$ $s^{-1}$, less than $2\times10^{-4}$ M$^{-1}$ s$^{-1}$, less than $3\times10^{-4}$ M$^{-1}$ s$^{-1}$, less than $4\times10^{-4}$ M$^{-1}$ s$^{-1}$, less than $5\times10^{-4}$ M$^{-1}$ s$^{-1}$, less than $7\times10^{-4}$ M$^{-1}$ s$^{-1}$, less than $8\times10^{-4}$ M$^{-1}$ s$^{-1}$, less than $9\times10^{-4}$ M$^{-1}$ s$^{-1}$, less than $1\times10^{-5}$ M$^{-1}$ s$^{-1}$, less than $2\times10^{-5}$ M$^{-1}$ s$^{-1}$, less than $3\times10^{-5}$ M$^{-1}$ s$^{-1}$, less than $4\times10^{-5}$ M$^{-1}$ s$^{-1}$, less than $5\times10^{-5}$ M$^{-1}$ s$^{-1}$, less than $6\times10^{-5}$ M$^{-1}$ s$^{-1}$, less than $7\times10^{-5}$ M$^{-1}$ s$^{-1}$, less than $8\times10^{-5}$ M$^{-1}$ s$^{-1}$, less than $9\times10^{-5}$ M$^{-1}$ s$^{-1}$, less than $1\times10^{-6}$ M$^{-1}$ s$^{-1}$, less than $2\times10$–$6$ M$^{-1}$ s$^{-1}$, less than $3\times10^{-6}$ M$^{-1}$ s$^{-1}$, less than $4\times10^{-6}$ M$^{-1}$ s$^{-1}$, less than $5\times10^{-6}$ M$^{-1}$ s$^{-1}$, less than $6\times10^{-6}$ M$^{-1}$ s$^{-1}$, less than $7\times10^{-6}$ M$^{-1}$ s$^{-1}$, less than $8\times10^{-6}$ M$^{-1}$ s$^{-1}$, less than $9\times10^{-6}$ M$^{-1}$ s$^{-1}$, or less than $1\times10^{-7}$ M$^{-1}$ s$^{-1}$. In certain embodiments, the $k_{on}$ can be determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the anti-TALEN antibodies bind TALEN proteins and/or the FokI catalytic domain with an dissociation rate ($k_{off}$) of less than $1\times10$'s$^{-1}$, less than $2\times10^{-2}$ s$^{-1}$, less than $3\times10^{-2}$ s$^{-1}$, less than $4\times10^{-2}$ s$^{-1}$, less than $5\times10^{-2}$ s$^{-1}$, less than $6\times10^{-2}$ s$^{-1}$, less than $7\times10^{-2}$ s$^{-1}$, less than $8\times10^{-2}$ s$^{-1}$, less than $9\times10^{-2}$ s$^{-1}$, less than $1\times10^{-3}$ s$^{-1}$, less than $2\times10^{-3}$ s$^{-1}$, less than $3\times10^{-3}$ s$^{-1}$, less than $4\times10^{-3}$ s$^{-1}$, less than $5\times10^{-3}$ s$^{-1}$, less than $6\times10^{-3}$ s$^{-1}$, less than $7\times10^{-3}$ s$^{-1}$, less than $8\times10^{-3}$ s$^{-1}$, less than $9\times10^{-3}$ s$^{-1}$, less than $1\times10^{-4}$ s$^{-1}$, less than $2\times10^{-4}$ s$^{-1}$, less than $3\times10^{-4}$ s$^{-1}$, less than $4\times10^{-4}$ s$^{-1}$, less than $5\times10^{-4}$ s$^{-1}$, less than $6\times10^{-4}$ s$^{-1}$ less than $7\times10^{-4}$ s$^{-1}$, less than $8\times10^{-4}$ s$^{-1}$, less than $9\times10^{-4}$ s$^{-1}$, less than $1\times10^{-5}$ s$^{-1}$, or less than $5\times10^{-4}$ s$^{-1}$. In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

Provided herein anti-TALEN antibodies bind TALEN proteins and/or the FokI catalytic domain, comprising a variable heavy chain (VH), wherein the amino acid sequence or polynucleotide sequence of the VH is selected from the VH sequences presented in Table 1a. The anti-TALEN antibodies that specifically bind to the FokI catalytic domain, comprising a variable heavy chain (VH), wherein the amino acid sequence or polynucleotide sequence of the VH is selected from the VH sequences presented in Table 1a. In some embodiments, the VH amino acid sequence is at least about 70%, at least about 75%, at least about 80%, at least about 85%, at least about 90%, at least about 95%, at least about 96%, at least about 97%, at least about 98%, at least about 99%, or about 100% identical to a VH sequence presented in Table 1a. Kabat CDR definitions are shown in bold and Chothia CDR definitions are underlined.

TABLE 1a

Heavy Chain Variable Regions (VH)

| Clone | VH Sequence | SEQ ID NO: |
|---|---|---|
| Amino Acid Sequence | | |
| 2299.2G3.C6 | QIQLVQSGPELKKPGETVKISCK ASGYTFTDYSIHWVKQAPGEGLK WMAWINTETGAPTFADDFKGRLA LSLETSANTAYLQINNLKHEDTA TYFCAKEGGFYFYAMDYWGQGTS VTVSS | 3 |
| 2299.5D4.C8 | QIQLVQSGPELKKPGETVKISCK ASGYTFTDYSIHWVKQAPGEGLK WMAWINTETGAPTFADDFKGRLA LSLETSANTAYLQINNLKHEDTA TYFCAKEGGFYFYAMDYWGQGTS VTVSS | 3 |
| 2299.6B3.B8.B6 | QIQLVQSGPELKKPGETVKISCK ASGYAFTDYSIHWMKQAPGEGLQ WMGWINTETAKPAFGDDFKGRFA FSLETSANTAHLHINNLRTEDTA TYFCAKEGGFYFYAMDYWGQGTS VTVSS | 4 |
| 2299.6G5.C7 | QIQLVQSGPELKKPGETVKISCK ASGYTFTDYSIHWVKQAPGKGLK WMGWINTETGAPTFADDFKGRFA FSLETSASTAFLQINNLKNEDTA TYFCAKEGGFYFYAMDYWGQGTS LTVSS | 5 |
| 2299.7F11.B4 | QIQLVQSGPELKKPGETVKISCK ASGYTFTDYSIHWVKQAPGKGLK WMAWINTETGDPTYEDDFKGRFA FSLETSASTAYLQINNLKNEDTA TYFCSKEGGFYFYAMDYWGQGTS VTVSS | 6 |
| Polynucleotide Sequence | | |
| 2299.2G3.C6 | CAGATCCAGTTGGTGCAGTCTGG ACCTGAGTTGAAGAAGCCTGGAG AGACAGTCAAGATCTCCTGCAAG GCTTCTGGTTATACCTTCACAGA CTATTCAATACACTGGGTGAAGC AGGCTCCAGGAGAGGGTTTAAAG TGGATGGCCTGGATAAACACTGA GACTGGTGCGCCAACATTTGCAG ATGACTTCAAGGGACGGTTAGCC CTCTCTTTGGAGACTTCTGCCAA CACTGCCTATTTGCAGATCAACA ACCTCAAACATGAAGACACGGCT ACATATTTCTGTGCTAAAGAAGG TGGTTTCTACTTTTATGCTATGG ACTACTGGGGTCAAGGAACCTCA GTCACCGTCTCCTCA | 29 |
| 2299.5D4.C8 | CAGATCCAGTTGGTGCAGTCTGG ACCTGAGTTGAAGAAGCCTGGAG AGACAGTCAAGATCTCCTGCAAG GCTTCTGGTTATACCTTCACAGA CTATTCAATACACTGGGTGAAGC AGGCTCCAGGAGAGGGTTTAAAG TGGATGGCCTGGATAAACACTGA GACTGGTGCGCCAACATTTGCAG ATGACTTCAAGGGACGGTTAGCC CTCTCTTTGGAGACCTCTGCCAA CACTGCCTATTTGCAGATCAACA ACCTCAAACATGAAGACACGGCA ACATATTTCTGTGCTAAAGAAGG TGGTTTCTACTTTTATGCTATGG ACTATTGGGGTCAAGGAACCTCA GTCACCGTCTCTTCA | 31 |
| 2299.6B3.B8.B6 | CAGATCCAGTTGGTGCAGTCTGG ACCTGAGCTGAAGAAGCCTGGAG AGACAGTCAAGATCTCCTGCAAG GCTTCTGGTTATGCCTTCACAGA CTATTCAATACACTGGATGAAGC AGGCTCCAGGAGAGGGTCTACAG TGGATGGGCTGGATAAACACTGA GACTGCTAAGCCAGCATTTGGAG ATGACTTCAAGGGACGGTTTGCC TTTTCTTTGGAAACCTCTGCCAA | 32 |

TABLE 1a-continued

Heavy Chain Variable Regions (VH)

| Clone | VH Sequence | SEQ ID NO: |
|---|---|---|
| | CACTGCCCATTTGCACATCAACA ACCTCAGAACTGAAGACACGGCT ACATATTTCTGTGCTAAAGAAGG TGGTTTCTACTTTTATGCTATGG ACTATTGGGGTCAAGGAACCTCA GTCACCGTCTCCTCA | |
| 2299.6G5.C7 | CAGATCCAGTTGGTGCAGTCTGG ACCTGAGTTGAAGAAGCCTGGAG AGACAGTCAAGATCTCCTGCAAG GCTTCTGGTTATACCTTCACAGA CTATTCAATACACTGGGTGAAGC AGGCTCCAGGAAAGGGTTAAAG TGGATGGGCTGGATAAACACTGA GACTGGTGCGCCAACATTTGCAG ATGACTTCAAGGGACGGTTTGCC TTCTCTTTGGAAACCTCTGCCAG CACTGCCTTTTGCAGATCAACA ACCTCAAAAATGAAGACACGGCT ACATATTTCTGTGCTAAGGAAGG TGGTTTCTACTTTTACGCTATGG ACTACTGGGGTCAAGGAACCTCG CTCACCGTCTCCTCA | 33 |
| 2299.7F11.B4 | CAGATCCAGTTGGTGCAGTCTGG ACCTGAGCTGAAGAAGCCTGGAG AGACAGTCAAGATCTCCTGCAAG GCCTCTGGTTATACCTTCACAGA CTACTCAATACACTGGGTGAAGC AGGCTCCAGGAAAGGGTTAAAG TGGATGGCCTGGATAAACACTGA GACTGGTGACCCAACATATGAAG ATGACTTCAAGGGACGGTTTGCC TTCTCTTTGGAAACCTCTGCCAG CACTGCCTATTGCAGATCAACA ACCTCAAAAATGAGGACACGGCT ACATATTTCTGTTCTAAAGAAGG TGGTTTCTACTTTTATGCTATGG ACTACTGGGGTCAAGGAACCTCA GTCACCGTCTCCTCA | 34 |

Provided herein are anti-TALEN antibodies that specifically bind to the Fok1 catalytic domain, comprising a variable light chain (VL), wherein the amino acid sequence or polynucleotide sequence of the VL is selected from the VL sequences presented in Table 1b. In some embodiments, the VL amino acid sequence is at least about 70%, at least about 75%, at least about 80%, at least about 85%, at least about 90%, at least about 95%, at least about 96%, at least about 97%, at least about 98%, at least about 99%, or about 100% identical to a VL sequence presented in Table 1b. Kabat CDR definitions are shown in bold and Chothia CDR definitions are underlined.

TABLE 1b (i) Light Chain Variable Regions (VL)

| Clone | VL Sequence | SEQ ID NO: |
|---|---|---|
| Amino Acid Sequence | | |
| 2299.2G3.C6 | DIVMSQSPSSRAVSAGEKVTMSC KSSQSLLSSRTRKNYLAWYQQKP GQAPKMLISWASTREFGVPDRFT GSGFGTDFTLTISSVQGEDLAVY YCKQSYNFRTFGGGTKLEIK | 7 |
| 2299.5D4.C8 | DIVMSQSPSSLAVSAGEKVTMSC KSSQSLLSSRTRKNYLAWYQQKP GQAPKLLISWASTRESGVPDRFT GSGSGTEFTLTISSVQAEDLAVY YCKQSYNLRTFGGGTKLEIK | 8 |
| 2299.6B3.B8.B6 | DIVMSQSPSSLAVSAGEKVTMNC KSSQSLLSSRTRKNYLAWYQQKP GQSPKLLIYWASTRDSGVPDRFT GSGSGTDFTLTISSVQAEDLAVY YCKQSYNFRTFGGGTKLEIK | 9 |
| 2299.6G5.C7 | DIVMSQSPSSLAVSTGEKVTMSC KSSQSLLSSRTRKNYLAWYQQKP GQAPKLLISWASTRESGVPDRFT GSGSGTDFTLTISSVQAEDLAVY YCKQSFNLRTFGGGTKLEIK | 10 |
| 2299.7F11.B4 | DIVMSQSPSSLAVSAGEKVTMSC KSSQSLLSSRTRKNYLAWYQQKP GQSPKLLIKWASTRESGVPDRFT GSGSGTDFTLTISSVQAEDLAVY YCKQSYNLRTFGGGTKLEIK | 11 |
| Polynucleotide Sequence | | |
| 2299.2G3.C6 | GACATTGTGATGTCACAGTCTCC ATCCTCCCGGGCTGTGTCAGCAG GAGAGAAGGTCACTATGAGCTGC AAATCCAGTCAGAGTCTGCTCAG CAGTCGAACCCGAAAGAACTACT TGGCTTGGTACCAACAGAAACCA GGGCAGGCTCCTAAAATGCTGAT TTCCTGGGCATCCACTAGGGAAT TTGGGGTCCCTGATCGCTTCACA GGCAGTGGATTTGGGACAGATTT CACTCTCACCATTAGCAGTGTGC AGGGTGAGGACCTGGCAGTTTAT TACTGCAAACAATCTTATAATTT TCGGACGTTCGGTGGAGGCACCA AGCTGGAAATCAAA | 30 |
| 2299.5D4.C8 | GACATTGTGATGTCACAGTCTCC ATCCTCCCTGGCTGTGTCAGCAG GAGAGAAGGTCACTATGAGCTGC AAGTCCAGTCAGAGTCTGCTCAG CAGTCGAACCCGAAAGAACTACT TGGCTTGGTACCAACAGAAACCA GGGCAGGCTCCTAAACTGCTGAT CTCCTGGGCATCCACTAGGGAAT CTGGGGTCCCTGATCGCTTCACA GGCAGTGGATCTGGGACAGAATT CACTCTCACCATCAGCAGTGTGC AGGCTGAGGACCTGGCAGTTTAT TACTGCAAACAATCTTATAATCT TCGGACGTTCGGTGGAGGCACCA AGCTGGAAATCAAA | 35 |
| 2299.6B3.B8.B6 | GACATTGTGATGTCACAGTCTCC ATCCTCCCTGGCTGTGTCAGCAG GAGAGAAGGTCACTATGAACTGC AAATCCAGTCAGAGTCTGCTCAG CAGTAGAACCCGAAAGAACTACT TGGCTTGGTACCAGCAGAAACCA GGGCAGTCTCCTAAACTGCTGAT CTACTGGGCTTCCACTAGGGACT CTGGGGTCCCTGATCGCTTCACA GGCAGTGGATCTGGGACAGATTT CACTCTCACCATCAGCAGTGTGC AGGCAGAGGACCTGGCAGTTTAT TACTGCAAGCAATCTTATAATTT TCGGACGTTCGGTGGAGGCACCA AGCTGGAAATCAAA | 36 |

TABLE 1b-continued (i) Light Chain Variable Regions (VL)

| Clone | VL Sequence | SEQ ID NO: |
|---|---|---|
| 2299.6G5.C7 | GACATTGTGATGTCACAGTCTCCATCCTCCCTGGCTGTATCAACAGGAGAGAAGGTCACTATGAGCTGCAAATCCAGTCAGAGTCTGCTCAGCAGTCGAACCCGAAAGAACTACTTGGCTTGGTACCAACAGAAACCAGGGCAGGCTCCTAAACTGCTGATCTCCTGGGCATCCACTAGGGAATCTGGGGTCCCTGATCGCTTCACAGGCAGTGGATCTGGGACAGATTTCACTCTCACCATCAGCAGTGTGCAGGCTGAAGACCTGGCAGTTTATTACTGCAAACAATCTTTTAATCTTCGGACGTTCGGTGGAGGCACCAAACTGGAAATCAAA | 37 |
| 2299.7F11.B4 | GACATTGTGATGTCACAGTCTCCATCCTCCCTGGCTGTGTCAGCAGGAGAGAAGGTCACTATGAGCTGCAAATCCAGTCAGAGTCTGCTCAGCAGTAGAACCCGAAAGAACTACTTGGCTTGGTACCAGCAGAAACCAGGGCAGTCTCCTAAACTGCTGATTAAATGGGCATCCACTAGGGAATCTGGGGTCCCTGATCGCTTCACAGGCAGTGGATCTGGGACAGATTTCACTCTCACCATCAGCAGTGTGCAGGCTGAAGACCTGGCAGTTTATTACTGCAAGCAATCTTATAATCTTCGGACGTTCGGTGGAGGCACCAAGCTGGAAATCAAA | 38 |

Provided herein are anti-TALEN antibodies that specifically bind to the Fok1 catalytic domain, wherein anti-TALEN antibodies comprise a variable heavy chain (VH) and a variable light chain (VL), wherein the amino acid sequence or polynucleotide sequence of the VH is selected from the VH sequences presented in Table 1a; and wherein the amino acid sequence or polynucleotide sequence of the VL is selected from the VL sequences presented in Table 1b.

In some embodiments, the anti-TALEN antibodies that specifically bind to the Fok1 catalytic domain, comprise a VH CDR 1, CDR2, and CDR3 of a VH sequence presented in Table 1a. In some embodiments, the VH CDR 1, CDR2, and CDR3 are selected from a CDR sequence presented in Table 1c.

TABLE 1c (ii) Heavy Chain CDRs

| Clone | CDR1 VH Sequence (Chothia) | SEQ ID NO: | CDR1 VH Sequence (Kabat) | SEQ ID NO: |
|---|---|---|---|---|
| 2299.2G3.C6 | GYTFTDY | 12 | DYSIH | 14 |
| 2299.5D4.C8 | GYTFTDY | 12 | DYSIH | 14 |
| 2299.6B3.B8.B6 | GYAFTDY | 13 | DYSIH | 14 |
| 2299.6G5.C7 | GYTFTDY | 12 | DYSIH | 14 |
| 2299.7F11.B4 | GYTFTDY | 12 | DYSIH | 14 |

TABLE 1c-continued (ii) Heavy Chain CDRs

| Clone | CDR2 VH Sequence (Chothia) | SEQ ID NO: | CDR2 VH Sequence (Kabat) | SEQ ID NO: |
|---|---|---|---|---|
| 2299.2G3.C6 | NTETGA | 15 | WINTETGAPTFADDFKG | 18 |
| 2299.5D4.C8 | NTETGA | 15 | WINTETGAPTFADDFKG | 18 |
| 2299.6B3.B8.B6 | NTETAK | 16 | WINTETAKPAFGDDFKG | 19 |
| 2299.6G5.C7 | NTETGA | 15 | WINTETGAPTFADDFKG | 18 |
| 2299.7F11.B4 | NTETGD | 17 | WINTETGDPTYEDDFKG | 20 |

| Clone | CDR3 VH Sequence (Chothia) | SEQ ID NO: | CDR3 VH Sequence (Kabat) | SEQ ID NO: |
|---|---|---|---|---|
| 2299.2G3.C6 | EGGFYFYAMDY | 21 | EGGFYFYAMDY | 21 |
| 2299.5D4.C8 | EGGFYFYAMDY | 21 | EGGFYFYAMDY | 21 |
| 2299.6B3.B8.B6 | EGGFYFYAMDY | 21 | EGGFYFYAMDY | 21 |
| 2299.6G5.C7 | EGGFYFYAMDY | 21 | EGGFYFYAMDY | 21 |
| 2299.7F11.B4 | EGGFYFYAMDY | 21 | EGGFYFYAMDY | 21 |

In some embodiments, anti-TALEN antibodies that specifically bind to the Fok1 catalytic domain, comprise a VL CDR 1, CDR2, and CDR3 of a VL sequence presented in Table 1b. In some embodiments, the VH CDR 1, CDR2, and CDR3 are selected from a CDR sequence presented in Table 1d.

TABLE 1d (iii) Light Chain CDRs

| Clone | CDR1 VL Sequence (Kabat and Chothia) | SEQ ID NO: |
|---|---|---|
| 2299.2G3.C6 | KSSQSLLSSRTRKNYLA | 22 |
| 2299.5D4.C8 | KSSQSLLSSRTRKNYLA | 22 |
| 2299.6B3.B8.B6 | KSSQSLLSSRTRKNYLA | 22 |
| 2299.6G5.C7 | KSSQSLLSSRTRKNYLA | 22 |
| 2299.7F11.B4 | KSSQSLLSSRTRKNYLA | 22 |

| Clone | CDR2 VL Sequence (Kabat and Chothia) | SEQ ID NO: |
|---|---|---|
| 2299.2G3.C6 | WASTREF | 23 |
| 2299.5D4.C8 | WASTRES | 24 |
| 2299.6B3.B8.B6 | WASTRDS | 25 |
| 2299.6G5.C7 | WASTRES | 24 |
| 2299.7F11.B4 | WASTRES | 24 |

TABLE 1d-continued (iii) Light Chain CDRs

| Clone | CDR3 VL Sequence (Kabat and Chothia) | SEQ ID NO: |
|---|---|---|
| 2299.2G3.C6 | KQSYNFRT | 26 |
| 2299.5D4.C8 | KQSYNLRT | 27 |
| 2299.6B3.B8.B6 | KQSYNFRT | 26 |
| 2299.6G5.C7 | KQSFNLRT | 28 |
| 2299.7F11.B4 | KQSYNLRT | 27 |

Practice of the methods, as well as preparation and use of the compositions disclosed herein employ, unless otherwise indicated, conventional techniques in molecular biology, biochemistry, computational chemistry, protein engineering, antibody structure and function, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001 and subsequent editions; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998 and subsequent editions.

Genome Editing Technologies

Transcription Activator-Like Effector Nucleases

Transcription activator-like effector nucleases (TALEN) typically refer to restriction enzymes that can be engineered to cut specific sequences of DNA. They generally include a TAL effector DNA-binding domain and a DNA cleavage domain, i.e., a nuclease which cuts DNA strands. Transcription activator-like effectors (TALEs) can be engineered to bind practically any desired DNA sequence. Thus, TALENs can be introduced into cells, for use in gene editing or for genome editing in situ.

Various non-specific DNA cleavage domain can be used in TALEN constructs including, but not limited to, wild-type FokI cleavage domain, portions of the FokI endonuclease, FokI cleavage domain variants such as those with mutations designed to improve cleavage specificity and cleavage activity. In some embodiments, a FokI domain functions as a dimer, involving two constructs with DNA binding domains for sites in a target genome with proper orientation and spacing. In some embodiments, the TALEN comprises an endonuclease (e.g., FokI) cleavage domain or cleavage half-domain. The disclosed antibodies can be used for any TALEN-mediated gene editing, including targeted integration; methods and compositions for nuclease-mediated targeted integration are described in WO2015127439A1, which is incorporated by reference in its entirety.

Zinc Finger Nucleases

Zinc finger nucleases (ZFNs) are protein chimera comprised of a zinc finger-based DNA-binding domain and a DNA-cleavage (i.e. nuclease) domain (e.g., FokI). ZFNs are able to introduce double-strand breaks (DSB; breaks at the same or very close points in both strands of a double-stranded DNA molecule) at specific locations within a DNA molecule which can subsequently be used to disable, replace, insert or edit a targeted genomic region.

Zinc fingers are among the most common DNA binding motifs found in eukaryotes. These proteins are classified according to the number and position of the cysteine and histidine residues available for zinc coordination. A zinc finger consists of two antiparallel β strands, and an α helix. The zinc ion is crucial for the stability of this domain type—in the absence of the metal ion the domain unfolds as it is too small to have a hydrophobic core. One very well-explored subset of zinc-fingers (the $C_2H_2$ class) comprises a pair of cysteine residues in the beta strands and two histidine residues in the alpha helix which are responsible for binding a zinc ion. The two other classes of zinc finger proteins are the $C_4$ and $C_6$ classes. Zinc fingers are important in regulation because when interacted with DNA and zinc ion, they provide a unique structural motif for DNA-binding proteins. The structure of each individual finger is highly conserved and consists of about 30 amino acid residues, constructed as a ββα fold and held together by the zinc ion. The α-helix occurs at the C-terminal part of the finger, while the β-sheet occurs at the N-terminal part.

The DNA-binding domain of a ZFN can be composed of two to eight zinc finger motifs due to their supposed modularity. In some embodiments, a ZFN comprises 2, 3, 4, 5, 6, 7, or 8 zinc finger motifs. Each zinc finger motif is typically considered to recognize and bind to a three-base pair sequence and as such, a protein including more zinc fingers targets a longer sequence and therefore has a greater specificity and affinity to the target site. Methods to engineer zinc finger binding domains to bind to a sequence of choice are well known in the art. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. Zinc finger engineering methods known in the art include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261. Depending upon the required specifications of the end-product, the included zinc fingers can be selected via a parallel, sequential or bipartite technique or through an in vitro cell-based technique. Exemplary selection methods are also known in the art, including phage display and two-hybrid systems, see, U.S. Pat. Nos. 5,789, 538; 5,925,523; 6,007,988; 6,013,453; 6,410,248; 6,140, 466; 6,200,759; and 6,242,568; and international patent publications WO 98/37186; WO 98/53057; WO 00/27878; and WO 01/88197. Enhancements of binding specificity for zinc finger binding domains have been previously described, for example, in WO 02/077227.

The non-specific nuclease domain of FokI is functionally independent of its natural DNA-binding domain and therefore can be employed in the construction of ZFNs. Since the domain must dimerize to accomplish a double-strand break it is necessary that a nuclease is also bound to the opposite strand by virtue of another ZFN molecule bound to its target sequence as shown in the diagram. The two target sites need not be the same, so long as ZFNs targeting both sites are present. In order to form a dimer, two ZFN molecules must meet with their respective recognition sites not less than 4-6 base pairs apart but also not so far apart that they may not dimerize. While one ZFN molecule binds its target sequence on one strand, another ZFN molecule binds its target sequence on the opposite strand, as shown in the diagram. The nuclease domains dimerize and each cleaves its own strand, producing a DSB. FokI can be employed as a homo- or a heterodimer. In some embodiments, FokI is a homodimer. In some embodiments, FokI is a heterodimer.

RNA-Guided FokI Nuclease

RNA-guided FokI nucleases (RFNs) are protein chimera comprised of a Cas9 nuclease (Cas9) DNA-binding domain and a DNA-cleavage domain (e.g., FokI-cleavage domain). RFNs specifically target particular DNA sequences through the use of a guide RNA (gRNA) bearing 17-20 nucleotides of target site complementarity at the 5' end. RFNs require dimerization of the FokI DNA cleavage domain to introduce double-strand breaks (DSB; breaks at the same or very close points in both strands of a double-stranded DNA molecule) at specific locations within a DNA molecule which can subsequently be used to disable, replace, insert or edit a targeted genomic region.

CRISPR

CRISPR-associated Cas systems have evolved in bacteria and archaea to use short RNAs to guide DNA cleavage complexes to specific nucleotide sequences. The CRISPR/Cas system has been adapted for genome editing in eukaryotic cells. Cas9 unwinds DNA and checks for complementarity to the 20 base pair spacer region of the gRNA thus specifically targeting DNA sequences preceding protospacer adjacent motifs (PAM) sequences in mammalian cell genomes. The introduction of DSBs allows for target sequence alteration through one of two endogenous DNA repair mechanisms—either non-homologous end-joining (NHEJ) or homology-directed repair (HDR). The CRISPR/Cas system has also been used for gene regulation including transcription repression and activation without altering the target sequence. Targeted gene regulation based on the CRISPR/Cas system uses an enzymatically inactive Cas9 (dCas9). Additional Cas9 descriptions and gRNA requirements for programmable dCas9 are incorporated in but not limited to U.S. patent Ser. Nos. 14/536,319, 14/320,498, and 14/320,467

Genome Editing Systems

As described above, TALENs, ZFNs and RFNs can bind to and cleave at targeted sites in a genome, permitting the insertion or deletion of specific DNA sequences, notably when a repair template is provided. Selective cutting is achieved through sequence specific targeting by the DNA binding domain (e.g., TAL effector DNA-binding domain) and DNA cleavage by FokI nucleases. After the TALEN construct creates a double stranded break at the target locus, the homologous recombination machinery searches for homology between the damaged chromosome and the extra-chromosomal fragment and copies the sequence of the fragment between the two broken ends of the chromosome, regardless of whether the fragment contains the original sequence, resulting in insertion of the gene of interest into the genome.

In addition to homology-mediated gene editing the TALEN approach can also be applied to gene editing (knock outs and insertions) mediated by non-homologous end joining.

In some embodiments, the genome editing system includes 1, 2, 3, 4, 5, 6, 7, 8 or more nucleic acid construct(s) encoding a "half-TALEN" which assemble to form a complete TALEN with targeted FokI-mediated nuclease activity. In some embodiments, the genome editing system includes two or four nucleic acid constructs encoding "half-TALENs" with targeted FokI-mediated nuclease activity. In some embodiments, the nucleic acids encode dimeric TALENs, or a TALEN comprising two "half-TALENs".

In some embodiments, a genome editing system includes a polynucleotide construct bearing a donor sequence which undergoes genomic insertion after nuclease cleavage. In some embodiments, a donor sequence will have one or more homologous region(s) that share identity to a genomic sequence with which recombination is desired. In some embodiments, a donor sequence will have one or more homologous region(s) that have at least 50% sequence identity to a genomic sequence with which recombination is desired. In some embodiments, 60%, 70%, 80%, 90%, 95%, 98%, 99%, or 99.9% sequence identity is present over a homologous region. Any value between 1% and 100% sequence identity can be present, depending upon the length of the donor polynucleotide.

In some embodiments, as part of gene therapy, DNA can be introduced into selected target cells in a manner such that the donor DNA is expressed, and a therapeutic product encoded thereby is produced. Additionally, or alternatively, donor DNA can in some manner mediate expression of DNA that encodes the therapeutic product, or it can encode a product, such as a peptide or RNA that in some manner mediates, directly or indirectly, expression of a therapeutic product. In some embodiments the donor DNA encodes a therapeutic product for the treatment or prevention of disease or disorder that results from a genetically defect or deficiency. In some embodiments, the donor DNA encodes a therapeutic product for the treatment or prevention of cancer or any other disease or disorder that results from a genetic defect or deficiency. In some embodiments, the donor DNA encodes a chimeric antigen receptor (CAR).

Techniques and protocols for genome editing are described in the art. See, for example, US 2005/0215502; US 2007/0134796; WO 2005/084190; WO2014204578, Urnov et al., Nature Reviews Genetics 11, 636-646 (2010); Rahman et al., Human Gene Therapy 22(8): 925-933 (2011); Tsai et al., Nature Biotechnology (2014) 32: 569-576; and Collins et al., Proceedings Biological Sciences/The Royal Society, 282 (1821):pii 20143003 (2015). For example, genome editing can be performed in vivo or ex vivo (e.g. in vitro). In some embodiments, viral and non-viral based gene transfer methods can be used to introduce nucleic acids encoding TALENs, ZFNs or RFNs into mammalian cells or target tissues. Such methods can be used to administer nucleic acids encoding TALENs, ZFNs or RFNs to cells in vitro. In some embodiments, non-viral vector delivery systems include DNA plasmids, naked nucleic acid, and nucleic acid complexed with a delivery vehicle such as poloxamers or liposomes. In some embodiments, the nucleic acids encoding TALENs, ZFNs or RFNs are transfected via electroporation. In some embodiments, the non-viral delivery system includes direct transfer of TALEN-, ZFN- or RFN-encoding mRNA, such as by microinjection. Viral vector delivery systems include DNA and RNA viruses, which have either episomal or integrated genomes after delivery to the cell. Examples of viral vector delivery systems include, but are not limited to, integrase-deficient lentiviral vectors, adenoviral vectors, and vectors based on adeno-associated virus. In some embodiments, components of the genome editing system are mixed prior to administering to a subject. In some embodiments, components of the genome editing system are administered separately. Separate administration of the genome editing components can be essentially simultaneous, sequential or separated by a determined period of time.

Described herein, are highly sensitive and reliable methods for detecting and/or measuring FokI in a sample. As shown herein, these methods can detect FokI at physiological levels.

Detection Moieties

Detection moieties as used herein include moieties of any structure capable of being detected by any methods known in the art. A detection moiety refers to any element, molecule, functional group, compound, fragment or moiety that is detectable. Detection moieties include, but are not limited to, radionuclides (e.g., $^3$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes (such as, for example fluorescein dyes, acridine dyes, SYBR dyes, rhodamine dyes, oxazine dyes, etc.), chemiluminescent agents (such as, for example, acridinum esters, stabilized dioxetanes, and the like), electrochemiluminescent agents (such as, for example, Sulfo Tags), bioluminescent agents (such as, for example, luciferin), spectrally resolvable inorganic fluorescent semiconductors nanocrystals (i.e., quantum dots), metal nanoparticles (e.g., gold, silver, copper, platinum, etc.), nanoclusters, paramagnetic metal ions, enzymes (such as, for example, horseradish peroxidase, alkaline phosphatase, etc.), colorimetric labels (such as, for example, dyes, colloidal gold, and the like), biotin, dioxigenin, haptens, and proteins for which antisera or monoclonal antibodies are available.

In some embodiments, the anti-FokI antibody is associated with a detection moiety. The anti-FokI antibody can be covalently or non-covalently associated with the detection moiety. In some embodiments the detection moiety is selected from sulfo-tag, horseradish peroxidase, alkaline phosphatase, FITC, digoxigenin, acridan, RPE, luciferin, fluorophores, chromophores, radioisotopes, or biotin.

In some embodiments, the detection moiety is an electrochemiluminescent (ECL) label. In general, ECL-based assays involve the use of electrochemiluminescent compounds as labels (referred to herein as ECL labels). Any compounds capable of electrochemiluminescence can be used as an ECL labels. Examples of ECL labels include, but are not limited to, organometallic compounds such as the tris-bipyridyl-ruthenium (RuBpy) moiety where the metal is from, for example, the metals of group VII and VIII, including Re, Ru, Ir and Os. In some embodiments, the ECL label is a Sulfo-Tag label. Species that react with the ECL label in the ECL process are referred to herein as ECL coreactants. Commonly used coreactants for ECL include tertiary amines (e.g. tripropylamine (TPA)), oxalate, and persulfate.

In some embodiments, the anti-TALEN antibody is associated with a detection moiety. The detection moiety can be associated with the anti-TALEN antibody through covalent conjugation or through non-covalent association. Covalent conjugation of the detection moiety to the anti-TALEN antibody can be direct or can be through a linker. In some embodiments the detection moiety is selected from an ECL tag (e.g., Sulfo-Tag), horseradish peroxidase, alkaline phosphatase, FITC, digoxigenin, acridan, RPE, luciferin, fluorophores, chromophores, radioisotopes, or biotin.

The anti-TALEN antibodies described herein can be used in any assay known in the art to measure presence or intensity of a detection moiety in immunoassays. In some embodiments, detecting the presence or absence of a FokI comprising molecule (e.g., a TALEN protein) comprises measurement of electrochemiluminescence, luminescence, fluorescence, or absorbance by any means known in the art. The detecting step can involve a quantitative measurement, which can be used to determine the amount of FokI polypeptide in the sample. Measurement(s) to determine the presence or intensity of FokI can be performed by a hand method or can be carried out using an apparatus such as an analyzer. For example, in some embodiments, the detection moiety can produce a color output. Methods can include visual appearance of a colored product and/or an instrument such as an analyzer can be used to detect or quantify the color product. In some embodiments, the detecting step comprises a measurement of electrochemiluminescence, which can be performed using a commercially available instrument.

In some embodiments, the detection moiety is a fluorescent label, a photochromic compound, a proteinaceous fluorescent label, a magnetic label, a radiolabel, or a hapten. In some embodiments, the detectable label is a fluorescent label is selected from the group consisting of an Atto dye, an Alexa Fluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2, mStrawberry, TurboFP602, AsRed2, mRFP1, J-Red, R-phycoerythrin (RPE), B-phycoeryhring (BPE), mCherry, HcRed1, Katusha, P3, Peridinin Chlorophyll (PerCP), mKate (TagFP635), TurboFP635, mPlum, and mRaspberry.

Type-2 Restriction Enzyme FokI

FokI is a bacterial type IIS restriction endonuclease that is naturally found in *Flavobacterium okeanokoites*. Natural FokI consists of an N-terminal DNA-binding domain and a non-specific DNA cleavage domain at the C-terminus. (UniProt Accession Number P14870) The full length wild type FokI amino acid sequence is:

```
                                          (SEQ ID NO: 2)
MFLSMVSKIRTFGWVQNPGKFENLKRVVQVFDRNSKVHNEVKNIKIPTLV

KESKIQKELVAIMNQHDLIYTYKELVGTGTSIRSEAPCDAIIQATIADQG

NKKGYIDNWSSDGFLRWAHALGFIEYINKSDSFVITDVGLAYSKSADGSA

IEKEILIEAISSYPPAIRILTLLEDGQHLTKFDLGKNLGFSGESGFTSLP

EGILLDTLANAMPKDKGEIRNNWEGSSDKYARMIGGWLDKLGLVKQGKKE

FIIPTLGKPDNKEFISHAFKITGEGLKVLRRAKGSTKFTRVPKRVYWEML

ATNLTDKEYVRTRRALILEILIKAGSLKIEQIQDNLKKLGFDEVIETIEN

DIKGLINTGIFIEIKGRFYQLKDHILQFVIPNRGVTKQLVKSELEEKKSE

LRHKLKYVPHEYIELIEIARNSTQDRILEMKVMEFFMKVYGYRGKHLGGS
```

```
RKPDGAIYTVGSPIDYGVIVDTKAYSGGYNLPIGQADEMQRYVEENQTRN

KHINPNEWWKVYPSSVTEFKFLFVSGHFKGNYKAQLTRLNHITNCNGAVL

SVEELLIGGEMIKAGTLTLEEVRRKFNNGEINF
```

The FokI DNA cleavage domain can function independently of the DNA binding domain. In some embodiments, a FokI polypeptide consists, consists essentially of or comprises the FokI nuclease domain. In some embodiments, the FokI catalytic domain polypeptide is wild-type amino acids 439-583 of SEQ ID NO: 2. In some embodiments, the anti-TALEN antibodies described herein bind to a molecule comprising SEQ ID NO:1.

```
                                              (SEQ ID NO: 1)
MKVMEFFMKVYGYRGKHLGGSRKPDGAIYTVGSPIDYGVIVDTKAYSGGY

NLPIGQADEMQRYVEENQTRNKHINPNEWWKVYPSSVTEFKFLFVSGHFK

GNYKAQLTRLNHITNCNGAVLSVEELLIGGEMIKAGTLTLEEVRRKFNNG

EINF
```

In some embodiments, the FokI protein is modified. In some embodiments, the modified FokI protein includes an amino acid sequence at least 80%, 85%, 90%, 95%, 96%, 97%, 98%, or 99% identical to wild-type FokI catalytic domain (SEQ ID NO:1). In some embodiments, the FokI protein comprises biologically active fragments of FokI. In some embodiments the biologically active fragment includes the catalytic domain of FokI. In some embodiments, FokI protein includes the DNA-cleavage domain of FokI. In some embodiments, the FokI protein comprises an amino acid sequences that differs from SEQ ID NO: 1 by 1, 2, 3, 4, 5, 6, 7, 8, 9, 10, 11, 12, 13, 14, 15, 20, or more amino acids.

Sample Types

Sample types of the present disclosure include any materials that have, are suspected to have, are likely to have, or are confirmed to have TALEN proteins or molecules comprising a FokI catalytic domain. In some embodiments, the sample is an in vitro sample. In some embodiments, the sample is an in vivo sample. In some embodiments, the sample is of biological origin (e.g., a biological sample). Biological samples include all materials that at one time were part of a living organism. In some embodiments, the biological sample is from a mammal. Mammals include, but are not limited to, humans, dogs, cats, cows, pigs, sheep, non-human primates and llamas. Humans can be of any age. The biological sample can take any form and include, but are not limited to, cells, tissue, whole blood, plasma, serum, urine, stool, saliva, cord blood, sperm, aqueous or vitreous humor, chorionic villus sample, and combination thereof. In some embodiments, the sample is a tissue sample, a blood sample, a formalin-fixed sample, a tissue grown ex vivo or cell culture media. In some embodiments, a sample e.g., a serum sample is to be analyzed for the presence (or absence) or level of TALEN or FokI protein.

Kits

Also provided herein are kits for use in detecting and/or measuring FokI in a sample (e.g., a biological sample), as described herein. Such kits typically comprise one or more substances, reagents and/or materials for use in the methods provided herein. The kit can include instructions for performing such methods. Kits for detecting and/or measuring FokI can include various reagents necessary for the analyzing 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, 1000 or more samples. In some embodiments, the kit can allow for the simultaneous or near simultaneous analysis of a plurality of samples, such as a microplate-type assay kit. In some embodiments, the kit can be disposable, such that reagents and materials are intended for a single use and/or to be disposed of after performance of the assay.

In some embodiments, a kit for use in detecting and/or measuring FokI in a sample comprises an anti-TALEN antibody described herein and optionally conjugated to a detection moiety, or can comprise materials allowing a used of the kit to perform such a conjugation. Substrates of the FokI detection kits described herein can take any suitable form that permits the association of anti-FokI antibodies described herein and FokI containing complexes. In some embodiments, the substrate is contained in or part of a microplate. Any suitable detection moiety known in the art can be used. For example, detection moieties include, but are not limited to, an ECL tag (e.g., Sulfo-Tag), horseradish peroxidase, alkaline phosphatase, FITC, digoxigenin, acridan, RPE, luciferin, fluorophores, chromophores, radioisotopes, or biotin. Further, any suitable methods of detection can be used in conjunction with FokI detection kits described herein. The kit may or may not include reagents, materials and or instruments for performing the detection or measurement of signal. In some embodiments, the use of a kit can include the detection of signal, which comprises measurement of electrochemiluminescence, luminescence, fluorescence, or absorbance. Detection of signal associated with an anti-FokI detection assay can be by any means known in the art. Associated kits may or may not include instructions for a specific detection method. In some embodiments, a kit can refer a user to standard methods of detection. In some embodiments, the kit can refer a user to follow instructions associated with other instrumentation for detection.

Representative Uses

In some embodiments, methods and kits of the present disclosure can be used for the evaluation and/or monitoring of cellular or gene therapy, such as CAR T therapy. In some embodiments the cellular or gene therapy is a ZFN-based gene therapy. In some embodiments, the cellular or gene therapy is a RFN-based gene therapy. In some embodiments, the cellular therapy is a TALEN-based gene therapy. In some embodiments, the cellular or gene therapy comprises the administration of a DNA construct. In some embodiments, the cellular or gene therapy comprises mRNA replacement therapy. In some embodiments, the cellular or gene therapy comprises cellular replacement therapy, such as Chimeric Antigen Receptor (CAR)-based therapy, which can comprise allogeneic or autologous cellular replacement. Cellular replacement therapy can comprise administering cells that have been transduced or transfected with a nucleic acid construct encoding a FokI protein or a biologically active fragment thereof.

In some embodiments, samples for evaluating and/or monitoring cellular or gene therapy can be obtained prior to the initiation of therapy. In some embodiments, samples are obtained after a first cellular or gene therapy treatment or dose. In some embodiments, samples are obtained after the conclusion of gene therapy. In some embodiments, samples are obtained at specific time points, intervals, or any other metric of time before, during or after cellular or gene therapy is performed. In some embodiments, FokI detection is used for assessing potential for cellular or gene therapy.

Methods of Treatment

In some embodiments, the anti-TALEN antibodies of the present disclosure can be used for the evaluation and/or monitoring of gene therapy or cellular replacement therapy, such as CAR therapy. In some embodiments, the gene therapy comprises administering to a patient a population of cells engineered with a TALEN protein to express a chimeric antigen receptor (CAR). The CAR containing immune cells can be used to treat malignancies involving aberrant expression of biomarkers, including cancer. In some embodiments, CAR containing immune cells of the disclosure can be used to treat non-Hodgkins lymphoma such as diffuse large B-cell lymphoma (DLBCL), leukemia (e.g., CLL or ALL), multiple myeloma (MM), small cell lung cancer, melanoma, low grade gliomas, glioblastoma, medullary thyroid cancer, carcinoids, dispersed neuroendocrine tumors in the pancreas, bladder and prostate, testicular cancer, and lung adenocarcinomas with neuroendocrine features.

As used herein, the term "cancer" includes, but is not limited to, solid tumors and blood-born tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastases, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin lymphoma, non-Hodgkin lymphoma (NHL), cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistant to chemotherapy or radiation. In a further embodiment a cancer has been reduced by a degree determined to be less than desire and a re-treatment is determined to be appropriate.

EXAMPLES

Example 1: Generation of Anti-TALEN Antibodies

To generate hybridoma cells, wildtype Balb/c mice were immunized with FokI catalytic domain protein including a C-terminal 6×His tag and GSGS linker. Using repetitive immunizations multiple sites (RIMMS), cells from immunization day 12 Balb/c mice were fused to obtain hybridoma fusion #2296. The resulting antibodies were screened on FokI catalytic domain for ELISA positives and counter screened using the His-tag antigen. Samples were also screened on full length TALEN protein including a C-terminal 6×His tag and GSGS linker. Antibodies were analyzed by Western Blot and assessed using Biacore® for binding confirmation and kinetics.

Antibodies obtained from fusion #2296 resulted in over 30 ELISA positives screened on FokI and full-length TALEN protein. These antibodies were negative on His-tag antigen. Biacore® analysis of fusion #2296 antibodies resulted in kD values ranging from 5 nM to 100 nM. The Biacore® kinetics of fusion #2296 RIMMS Day 12 are shown in Table 2 below.

TABLE 2

Biacore ® kinetics of Fusion 2296

| Ligand | Analyte | $k_a$ (1/Ms) | $k_d$ (1/s) | $t_{1/2}$ (min) | $K_D$ (nM) | Binds FokI or TALEN (Y/N/A) |
|---|---|---|---|---|---|---|
| A01_1A8 | FokI | 5.51E+03 | 3.51E−04 | 32.9 | 63.7 | Y |
| A01_1A8 | TALEN | | | | | Y |
| A02_7E12 | FokI | 2.72E+03 | 4.72E−04 | 24.5 | 174 | Y |
| A02_7E12 | TALEN | | | | | Y |
| A03_14H5 | FokI | 5.47E+04 | 7.09E−04 | 16.3 | 13.0 | Y |
| A03_14H5 | TALEN | | | | | Y |
| A05_1G2 | FokI | 7.87E+05 | 3.16E−02 | 0.4 | 40.2 | Y |
| A05_1G2 | TALEN | | | | | Y |
| B04_22A5 | FokI | 1.01E+06 | 4.62E−02 | 0.3 | 45.7 | Y |
| B04_22A5 | TALEN | | | | | Y |
| B05_2G3 | FokI | 1.18E+04 | 6.15E−04 | 18.8 | 52.1 | Y |
| B05_2G3 | TALEN | | | | | Y |
| C03_17B5 | FokI | 2.02E+05 | 5.01E−03 | 2.3 | 24.8 | Y |
| C03_17B5 | TALEN | | | | | Y |
| C04_22C12 | FokI | 1.83E+04 | 4.83E−04 | 23.9 | 26.4 | Y |
| C04_22C12 | TALEN | | | | | Y |
| D02_10B4 | FokI | 5.86E+05 | 4.36E−03 | 2.6 | 7.4 | Y |
| D02_10B4 | TALEN | | | | | Y |
| D04_23D1 | FokI | 2.63E+04 | 6.20E−04 | 18.6 | 23.6 | Y |
| D04_23D1 | TALEN | | | | | Y |
| E01_2D7 | FokI | 7.45E+05 | 1.48E−02 | 0.8 | 19.9 | Y |
| E01_2D7 | TALEN | | | | | Y |

TABLE 2-continued

Biacore ® kinetics of Fusion 2296

| Ligand | Analyte | $k_a$ (1/Ms) | $k_d$ (1/s) | $t_{1/2}$ (min) | $K_D$ (nM) | Binds FokI or TALEN (Y/N/A) |
|---|---|---|---|---|---|---|
| E02_10D7 | FokI | 5.15E+05 | 1.96E-02 | 0.6 | 38.1 | Y |
| E02_10D7 | TALEN | | | | | Y |
| G01_5E11 | FokI | 5.35E+05 | 2.01E-02 | 0.6 | 37.6 | Y |
| G01_5E11 | TALEN | | | | | Y |
| G02_11D2 | FokI | 1.59E+05 | 8.91E-04 | 13.0 | 5.6 | Y |
| G02_11D2 | TALEN | | | | | Y |
| G03_20F9 | FokI | 1.49E+06 | 4.65E-02 | 0.2 | 31.2 | Y |
| G03_20F9 | TALEN | | | | | Y |
| G04_1A1 | FokI | 5.00E+03 | 5.15E-04 | 22.4 | 103 | Y |
| G04_1A1 | TALEN | | | | | Y |
| H01_6H4 | FokI | 2.97E+05 | 1.87E-03 | 6.2 | 6.3 | Y |
| H01_6H4 | TALEN | | | | | Y |
| H02_13B2 | FokI | 1.06E+06 | 3.21E-02 | 0.4 | 30.3 | Y |
| H02_13B2 | TALEN | | | | | Y |

Hybridoma fusion #2299 cells were obtained from a long immunization on day 94. Balb/c mouse #2299 with higher antibody titer was selected for fusion. Antibodies obtained from fusion #2299 resulted in over 68 ELISA positives screened on FokI and full-length TALEN protein. These antibodies were negative on the His tag antigen. Biacore® analysis of fusion #2299 antibodies resulted in kD values ranging from sub nM to 100 nM. Five out of the top 12 ELISA binders were positive in Western Blot analysis with supernatant (FIG. 1). The Biacore® kinetics of exemplary antibodies from fusion #2299 are shown in Table 3 below.

TABLE 3

Biacore ® kinetics of Fusion 2299

| Ligand | Analyte | $k_a$ (1/Ms) | $k_d$ (1/s) | $t_{1/2}$ (min) | $K_D$ (nM) | Binds FokI or TALEN (Y/N/A) |
|---|---|---|---|---|---|---|
| D04_4C7 | FokI | 3.32E+05 | 1.26E-04 | 91.69 | 0.38 | Y |
| C09_9H1 | FokI | 5.72E+04 | 9.38E-05 | 123.16 | 1.64 | Y |
| A02_1G2 | FokI | 3.63E+04 | 6.12E-05 | 188.77 | 1.69 | Y |
| C02_1G12 | FokI | 5.94E+04 | 1.16E-04 | 99.59 | 1.95 | Y |
| A04_4B10 | FokI | 1.02E+05 | 2.33E-04 | 49.58 | 2.28 | Y |
| G02_2E5 | FokI | 1.10E+05 | 2.73E-04 | 42.32 | 2.48 | Y |
| E01_1D1 | FokI | 7.43E+04 | 1.91E-04 | 60.48 | 2.57 | Y |
| H08_8H12 | FokI | 2.39E+06 | 9.98E-03 | 1.16 | 4.18 | Y |
| B02_1G6 | FokI | 1.01E+05 | 4.36E-04 | 26.50 | 4.32 | Y |
| E02_2D 12 | FokI | 7.09E+04 | 3.29E-04 | 35.11 | 4.64 | Y |
| D01_1C10 | FokI | 7.47E+04 | 3.96E-04 | 29.17 | 5.30 | Y |
| G09_2299.8C5 | FokI | 1.58E+05 | 1.21E-03 | 9.55 | 7.66 | Y |
| F08_8F3 | FokI | 2.92E+04 | 2.59E-04 | 44.60 | 8.87 | Y |
| F09_2299.4D4.1 | FokI | 1.06E+04 | 1.39E-04 | 83.11 | 13.11 | Y |
| G07_7D2 | FokI | 9.06E+05 | 1.48E-02 | 0.78 | 16.34 | Y |
| B08_7G8 | FokI | 9.16E+05 | 1.51E-02 | 0.77 | 16.48 | Y |
| H05_6A6 | FokI | 6.65E+03 | 1.17E-04 | 98.74 | 17.59 | Y |
| F07_7B11 | FokI | 6.60E+05 | 1.75E-02 | 0.66 | 26.52 | Y |
| A01_1A4 | FokI | 7.66E+05 | 2.05E-02 | 0.56 | 26.76 | Y |
| A09_9D1 | FokI | 5.85E+05 | 2.74E-02 | 0.42 | 46.84 | Y |
| G04_4F11 | FokI | 6.99E+03 | 3.32E-04 | 34.80 | 47.50 | Y |
| H01_1F12 | FokI | 4.30E+03 | 2.10E-04 | 55.01 | 48.84 | Y |
| E07_7A11 | FokI | 5.23E+05 | 2.60E-02 | 0.44 | 49.71 | Y |
| H02_2E8 | FokI | 9.54E+03 | 4.78E-04 | 24.17 | 50.10 | Y |
| C03_3D1 | FokI | 5.27E+05 | 3.56E-02 | 0.32 | 67.55 | Y |
| E04_4D4 | FokI | 2.45E+05 | <8.55E-05 | >135 | <0.35 | Y |
| F04_4D12 | FokI | 2.42E+05 | <8.55E-05 | >135 | <0.35 | Y |
| C04_4C6 | FokI | 9.12E+04 | <8.55E-05 | >135 | <0.94 | Y |
| A08_7F11 | FokI | 7.57E+04 | <8.55E-05 | >135 | <1.13 | Y |
| D08_8D2 | FokI | 7.23E+04 | <8.55E-05 | >135 | <1.18 | Y |
| F05_5G9 | FokI | 6.45E+04 | <8.55E-05 | >135 | <1.33 | Y |
| E05_5F5 | FokI | 5.84E+04 | <8.55E-05 | >135 | <1.46 | Y |
| B04_4B11 | FokI | 4.81E+04 | <8.55E-05 | >135 | <1.78 | Y |
| C08_8C7 | FokI | 4.81E+04 | <8.55E-05 | >135 | <1.78 | Y |

Purified antibodies shown in Table 4 below were chosen for further analysis and assay development.

TABLE 4

Summary of antibody panel

| Ligand | Analyte | $k_a$ (1/Ms) | $k_d$ (1/s) | $t_{1/2}$ (min) | $K_D$ (nM) | Binds FokI or TALEN (Y/N/A) | ELISA | Western Blot |
|---|---|---|---|---|---|---|---|---|
| 2299.2G3.C6 | FokI | 1.77E+04 | <8.55E−05 | >135 | <4.83 | Y | + | + |
| 2299.5D4.C8 | FokI | 1.12E+04 | <8.55E−05 | >135 | <7.63 | Y | + | + |
| 2299.6B3.B8.B6 | FokI | 9.87E+03 | <8.55E−05 | >135 | <8.66 | Y | + | + |
| 2299.6G5.C7 | FokI | 5.27E+03 | <8.55E−05 | >135 | <16.2 | Y | + | + |
| 2299.7F11.B4 | FokI | 7.57E+04 | <8.55E−05 | >135 | <1.13 | Y | + | + |
| 2296.14H5.C10 | FokI | 1.39E+03 | 6.81E−04 | 16.96 | 489.93 | Y | +/− | − |
| 2296.17B5.A4 | FokI | 8.33E+04 | 9.40E−04 | 12.29 | 11.28 | Y | + | − |
| 2296.23D1.B2 | FokI | 2.31E+03 | 6.31E−04 | 18.31 | 273.16 | Y | +/− | − |

EQUIVALENTS AND SCOPE

Those skilled in the art will recognize, or be able to ascertain using no more than routine experimentation, many equivalents to the specific embodiments of the present disclosure as described herein. The scope of the present disclosure is not intended to be limited to the above description, but rather as set forth in the following claims.

What is claimed is:

1. An antibody specific for FokI nuclease catalytic domain comprising the amino acid sequence of SEQ ID NO:1, the antibody comprising a variable heavy chain (VH) amino acid sequence that is at least 85% identical to SEQ ID NO: 3 and a variable light chain (VL) amino acid sequence that is at least 90% identical to SEQ ID NO: 7.

2. The antibody of claim 1 comprising a VH amino acid sequence that is at least 90%, at least 95%, at least 96%, at least 97%, at least 98%, at least 99%, or 100% identical to SEQ ID NO: 3, or a VL amino acid sequence that is at least 96%, at least 97%, at least 98%, at least 99%, or 100% identical to SEQ ID NO: 7.

3. The antibody of claim 1, comprising
(a) a VH CDR1 comprising the amino acid sequence of SEQ ID NO:12 or 14;
(b) a VH CDR2 comprising the amino acid sequence of SEQ ID NO: 15 or 18;
(c) a VH CDR3 comprising the amino acid sequence of SEQ ID NO: 21;
(d) a VL CDR1 comprising the amino acid sequence of SEQ ID NO: 22;
(e) a VL CDR2 comprising the amino acid sequence of SEQ ID NO: 23; and
(f) a VL CDR3 comprising the amino acid sequence of SEQ ID NO: 26, or comprising
(g) a VH CDR1 comprising the amino acid sequence of SEQ ID NO: 13 or 14;
(h) a VH CDR2 comprising the amino acid sequence of SEQ ID NO: 16 or 19;
(i) a VH CDR3 comprising the amino acid sequence of SEQ ID NO: 21;
(j) a VL CDR1 comprising the amino acid sequence of SEQ ID NO: 22;
(k) a VL CDR2 comprising the amino acid sequence of SEQ ID NO: 25; and
(l) a VL CDR3 comprising the amino acid sequence of SEQ ID NO: 26, or comprising
(m) a VH CDR1 comprising the amino acid sequence of SEQ ID NO: 12 or 14;
(n) a VH CDR2 comprising the amino acid sequence of SEQ ID NO: 15 or 18;
(o) a VH CDR3 comprising the amino acid sequence of SEQ ID NO: 21;
(p) a VL CDR1 comprising the amino acid sequence of SEQ ID NO: 22;
(q) a VL CDR2 comprising the amino acid sequence of SEQ ID NO: 24; and
(r) a VL CDR3 comprising the amino acid sequence of SEQ ID NO: 28, or comprising
(s) a VH CDR1 comprising the amino acid sequence of SEQ ID NO: 12 or 14;
(t) a VH CDR2 comprising the amino acid sequence of SEQ ID NO: 17 or 20;
(u) a VH CDR3 comprising the amino acid sequence of SEQ ID NO: 21;
(v) a VL CDR1 comprising the amino acid sequence of SEQ ID NO: 22;
(w) a VL CDR2 comprising the amino acid sequence of SEQ ID NO: 24; and
(x) a VL CDR3 comprising the amino acid sequence of SEQ ID NO: 27, or comprising
(y) a VH CDR1 comprising the amino acid sequence of SEQ ID NO: 12 or 14;
(z) a VH CDR2 comprising the amino acid sequence of SEQ ID NO: 15 or 18;
(aa) a VH CDR3 comprising the amino acid sequence of SEQ ID NO: 21;

(bb) a VL CDR1 comprising the amino acid sequence of SEQ ID NO: 22;
(cc) a VL CDR2 comprising the amino acid sequence of SEQ ID NO: 24; and
(dd) a VL CDR3 comprising the amino acid sequence of SEQ ID NO: 27.

4. The antibody of claim 1, wherein the antibody further comprises a detectable label.

5. The antibody of claim 4, wherein the detectable label is selected from the group consisting of a fluorescent label, a photochromic compound, a proteinaceous fluorescent label, a magnetic label, a radiolabel, and a hapten.

6. The antibody of claim 5, wherein the fluorescent label is R-phycoerythrin (PE) or allophycocyanin (APC).

7. A composition comprising the antibody of claim 1 and a pharmaceutically acceptable carrier or vehicle.

8. A method of making the antibody of claim 1 comprising incubating a cell comprising one or more vectors comprising a polynucleotide encoding the heavy chain of the antibody of claim 1 and a polynucleotide encoding the light chain of the anitbody of claim 1 under suitable conditions.

9. A method of determining the presence of a FokI nuclease catalytic domain comprising the amino acid sequence of SEQ ID NO: 1 in a sample, the method comprising contacting the sample with the antibody of claim 1 conjugated to a detectable label and determining the presence of the FokI nuclease catalytic domain in the sample.

10. The method of claim 9, wherein the detectable label is selected from the group consisting of a fluorescent label, a photochromic compound, a proteinaceous fluorescent label, a magnetic label, a radiolabel, and a hapten.

11. The method of claim 9, wherein the sample is an immune cell sample, a tissue sample, a blood sample, a formalin-fixed sample, a tissue grown ex vivo or cell culture media.

12. The method of claim 10, wherein the sample is an immune cell sample, a tissue sample, a blood sample, a formalin-fixed sample, a tissue grown ex vivo or cell culture media.

13. The antibody of claim 3, comprising:
(a) a VH CDR1 comprising the amino acid sequence of SEQ ID NO:12 or 14;
(b) a VH CDR2 comprising the amino acid sequence of SEQ ID NO: 15 or 18;
(c) a VH CDR3 comprising the amino acid sequence of SEQ ID NO: 21;
(d) a VL CDR1 comprising the amino acid sequence of SEQ ID NO: 22;
(e) a VL CDR2 comprising the amino acid sequence of SEQ ID NO: 23; and
(f) a VL CDR3 comprising the amino acid sequence of SEQ ID NO: 26, and a VH comprising the amino acid sequence of SEQ ID NO: 3; and a VL comprising the amino acid sequence of SEQ ID NO: 7.

14. The antibody of claim 3, comprising:
(g) a VH CDR1 comprising the amino acid sequence of SEQ ID NO: 13 or 14;
(h) a VH CDR2 comprising the amino acid sequence of SEQ ID NO: 16 or 19;
(i) a VH CDR3 comprising the amino acid sequence of SEQ ID NO: 21;
(j) a VL CDR1 comprising the amino acid sequence of SEQ ID NO: 22;
(k) a VL CDR2 comprising the amino acid sequence of SEQ ID NO: 25; and
(l) a VL CDR3 comprising the amino acid sequence of SEQ ID NO: 26, and a VH comprising the amino acid sequence of SEQ ID NO: 4; and a VL comprising the amino acid sequence of SEQ ID NO: 9.

15. The antibody of claim 3, comprising:
(m) a VH CDR1 comprising the amino acid sequence of SEQ ID NO: 12 or 14;
(n) a VH CDR2 comprising the amino acid sequence of SEQ ID NO: 15 or 18;
(o) a VH CDR3 comprising the amino acid sequence of SEQ ID NO: 21;
(p) a VL CDR1 comprising the amino acid sequence of SEQ ID NO: 22;
(q) a VL CDR2 comprising the amino acid sequence of SEQ ID NO: 24; and
(r) a VL CDR3 comprising the amino acid sequence of SEQ ID NO: 28, and a VH comprising the amino acid sequence of SEQ ID NO: 5; and a VL comprising the amino acid sequence of SEQ ID NO: 10.

16. The antibody of claim 3, comprising:
(s) a VH CDR1 comprising the amino acid sequence of SEQ ID NO: 12 or 14;
(t) a VH CDR2 comprising the amino acid sequence of SEQ ID NO: 17 or 20;
(u) a VH CDR3 comprising the amino acid sequence of SEQ ID NO: 21;
(v) a VL CDR1 comprising the amino acid sequence of SEQ ID NO: 22;
(w) a VL CDR2 comprising the amino acid sequence of SEQ ID NO: 24; and
(x) a VL CDR3 comprising the amino acid sequence of SEQ ID NO: 27, and a VH comprising the amino acid sequence of SEQ ID NO: 6; and a VL comprising the amino acid sequence of SEQ ID NO: 11.

17. The antibody of claim 3, comprising:
(y) a VH CDR1 comprising the amino acid sequence of SEQ ID NO: 12 or 14;
(z) a VH CDR2 comprising the amino acid sequence of SEQ ID NO: 15 or 18;
(aa) a VH CDR3 comprising the amino acid sequence of SEQ ID NO: 21;
(bb) a VL CDR1 comprising the amino acid sequence of SEQ ID NO: 22;
(cc) a VL CDR2 comprising the amino acid sequence of SEQ ID NO: 24; and (dd)
a VL CDR3 comprising the amino acid sequence of SEQ ID NO: 27, and a VH comprising the amino acid sequence of SEQ ID NO: 3; and a VL comprising the amino acid sequence of SEQ ID NO: 8.

18. A method of determining the presence of a FokI nuclease catalytic domain comprising the amino acid sequence of SEQ ID NO:1 in a sample, the method comprising contacting the sample with the antibody of claim 16 and determining the presence of the FokI nuclease catalytic domain in the sample.

19. The method of claim 18, wherein the antibody is conjugated to a detectable label.

20. The method of claim 19, wherein the detectable label is selected from the group consisting of a fluorescent label, a photochromic compound, a proteinaceous fluorescent label, a magnetic label, a radiolabel, and a hapten.

21. The method of claim 18, wherein the sample is an immune cell sample, a tissue sample, a blood sample, a formalin-fixed sample, a tissue grown ex vivo or cell culture media.

22. The method of claim 19, wherein the sample is an immune cell sample, a tissue sample, a blood sample, a formalin-fixed sample, a tissue grown ex vivo or cell culture media.

23. A method of making the antibody of claim 3 comprising incubating a cell comprising one or more vectors comprising a polynucleotide encoding the heavy chain of the antibody of claim 3 and a polynucleotide encoding the light chain of the antibody of claim 3 under suitable conditions.

* * * * *